US010188381B2

(12) United States Patent
Kurd et al.

(10) Patent No.: US 10,188,381 B2
(45) Date of Patent: Jan. 29, 2019

(54) SUTURE REPAIR DEVICE

(71) Applicant: DURA TAP LLC, Wayne, PA (US)

(72) Inventors: Mark F. Kurd, Bryn Mawr, PA (US);
David Greg Anderson, Moorestown, NJ (US); Jaime E. Sarabia, Mableton, GA (US); Eric Buehlmann, Redwood City, CA (US)

(73) Assignee: Dura Tap LLC, Wayne, PA (US)

( * ) Notice: Subject to any disclaimer, the term of this patent is extended or adjusted under 35 U.S.C. 154(b) by 410 days.

(21) Appl. No.: 14/947,464

(22) Filed: Nov. 20, 2015

(65) Prior Publication Data
US 2017/0143331 A1 May 25, 2017

(51) Int. Cl.
*A61B 17/04* (2006.01)
*A61B 17/062* (2006.01)
(Continued)

(52) U.S. Cl.
CPC ........ *A61B 17/0469* (2013.01); *A61B 17/062* (2013.01); *A61B 2017/0023* (2013.01); *A61B 2017/0046* (2013.01); *A61B 2017/00367* (2013.01); *A61B 2017/00393* (2013.01); *A61B 2017/047* (2013.01);
(Continued)

(58) Field of Classification Search
CPC . A61B 17/0469; A61B 17/062; A61B 17/065; A61B 2017/047; A61B 2017/0046; A61B 2017/00393; A61B 2017/0472; A61B 2017/0479; A61B 2017/0474; A61B 2017/00367; A61B 2017/0023; A61B 2017/0608
See application file for complete search history.

(56) References Cited

U.S. PATENT DOCUMENTS

| 1,822,330 A | 9/1931 | Ainslie |
| 4,406,237 A | 9/1983 | Eguchi et al. |

(Continued)

FOREIGN PATENT DOCUMENTS

| WO | 2014/145381 | 9/2014 |
| WO | 2013/158622 | 10/2014 |

OTHER PUBLICATIONS

International Search Report filed in PCT/US2016/062454 dated Feb. 2, 2017.

*Primary Examiner* — Darwin Erezo
*Assistant Examiner* — Erich Herbermann
(74) *Attorney, Agent, or Firm* — Rankin, Hill & Clark LLP

(57) ABSTRACT

An apparatus includes a handle, a cartridge configured to removably couple to the handle, an actuator movably coupled to the handle, and a lock operably coupled to the actuator. A first needle assembly and a second needle assembly of the cartridge are operably coupled to a first coupling portion and a second coupling portion, respectively, of the actuator when the cartridge is coupled to the handle. The first coupling portion is configured to transition the first needle assembly from a first configuration to a second configuration such that a first capture portion engages a first needle. The second coupling portion is configured to transition the second needle assembly from a first configuration to a second configuration such that a second capture portion engages the second needle. The lock is configured to selectively limit movement of the first coupling portion and the second coupling portion.

29 Claims, 19 Drawing Sheets

(51) Int. Cl.
*A61B 17/00* (2006.01)
*A61B 17/06* (2006.01)

(52) U.S. Cl.
CPC ........... *A61B 2017/0472* (2013.01); *A61B 2017/0474* (2013.01); *A61B 2017/0479* (2013.01); *A61B 2017/0608* (2013.01)

(56) References Cited

U.S. PATENT DOCUMENTS

| | | | |
|---|---|---|---|
| 5,053,046 A | 10/1991 | Janese | |
| 5,320,632 A | 6/1994 | Heidmueller | |
| 5,364,408 A | 11/1994 | Gordon | |
| 5,368,601 A | 11/1994 | Sauer et al. | |
| 5,374,275 A | 12/1994 | Bradley et al. | |
| 5,387,221 A | 2/1995 | Bisgaard | |
| 5,458,609 A | 10/1995 | Gordon et al. | |
| 5,474,568 A * | 12/1995 | Scott | A61B 17/0469 112/169 |
| 5,527,321 A | 6/1996 | Hinchliffe | |
| 5,540,704 A | 7/1996 | Gordon et al. | |
| 5,540,705 A | 7/1996 | Meade et al. | |
| 5,571,119 A | 11/1996 | Atala | |
| 5,575,800 A | 11/1996 | Gordon | |
| 5,741,276 A | 4/1998 | Poloyko et al. | |
| 5,741,279 A | 4/1998 | Gordon et al. | |
| 5,938,668 A | 8/1999 | Scirica et al. | |
| 6,051,006 A | 4/2000 | Schluzas et al. | |
| 6,143,004 A | 11/2000 | Davis et al. | |
| 6,224,614 B1 | 5/2001 | Yoon | |
| 6,245,079 B1 * | 6/2001 | Nobles | A61B 17/0057 606/139 |
| 6,296,648 B1 | 10/2001 | Boche et al. | |
| 6,533,795 B1 | 3/2003 | Tran et al. | |
| 6,939,356 B2 | 9/2005 | Debbas | |
| 7,967,832 B2 | 6/2011 | Chu | |
| 7,993,354 B1 | 8/2011 | Brecher et al. | |
| 8,202,281 B2 | 6/2012 | Voss | |
| 8,246,638 B2 | 8/2012 | Perez-Cruet et al. | |
| 8,496,675 B2 | 7/2013 | Chambers | |
| 8,551,121 B2 | 10/2013 | Overes et al. | |
| 2008/0091220 A1 | 4/2008 | Chu | |
| 2009/0062816 A1 | 3/2009 | Weber | |
| 2009/0281556 A1 * | 11/2009 | Newell | A61B 17/0401 606/144 |
| 2010/0114182 A1 | 5/2010 | Wilcox et al. | |
| 2010/0130990 A1 | 5/2010 | Saliman | |
| 2011/0270282 A1 | 11/2011 | Lemke | |
| 2012/0016385 A1 | 1/2012 | Keren et al. | |
| 2012/0071896 A1 | 3/2012 | Ferree | |
| 2012/0283751 A1 | 11/2012 | Perez-Cruet et al. | |
| 2013/0030450 A1 | 1/2013 | Dreyfuss et al. | |
| 2013/0041388 A1 | 2/2013 | Lane et al. | |
| 2013/0072948 A1 | 3/2013 | States et al. | |
| 2013/0103056 A1 | 4/2013 | Chu | |
| 2013/0123814 A1 | 5/2013 | Chu | |
| 2013/0158569 A1 | 6/2013 | Chu et al. | |
| 2013/0211428 A1 | 8/2013 | Kortenbach et al. | |
| 2013/0231689 A1 | 9/2013 | Binmoeller et al. | |
| 2013/0267967 A1 | 10/2013 | Fortson et al. | |
| 2015/0088167 A1 * | 3/2015 | Chin | A61B 17/0482 606/145 |

* cited by examiner

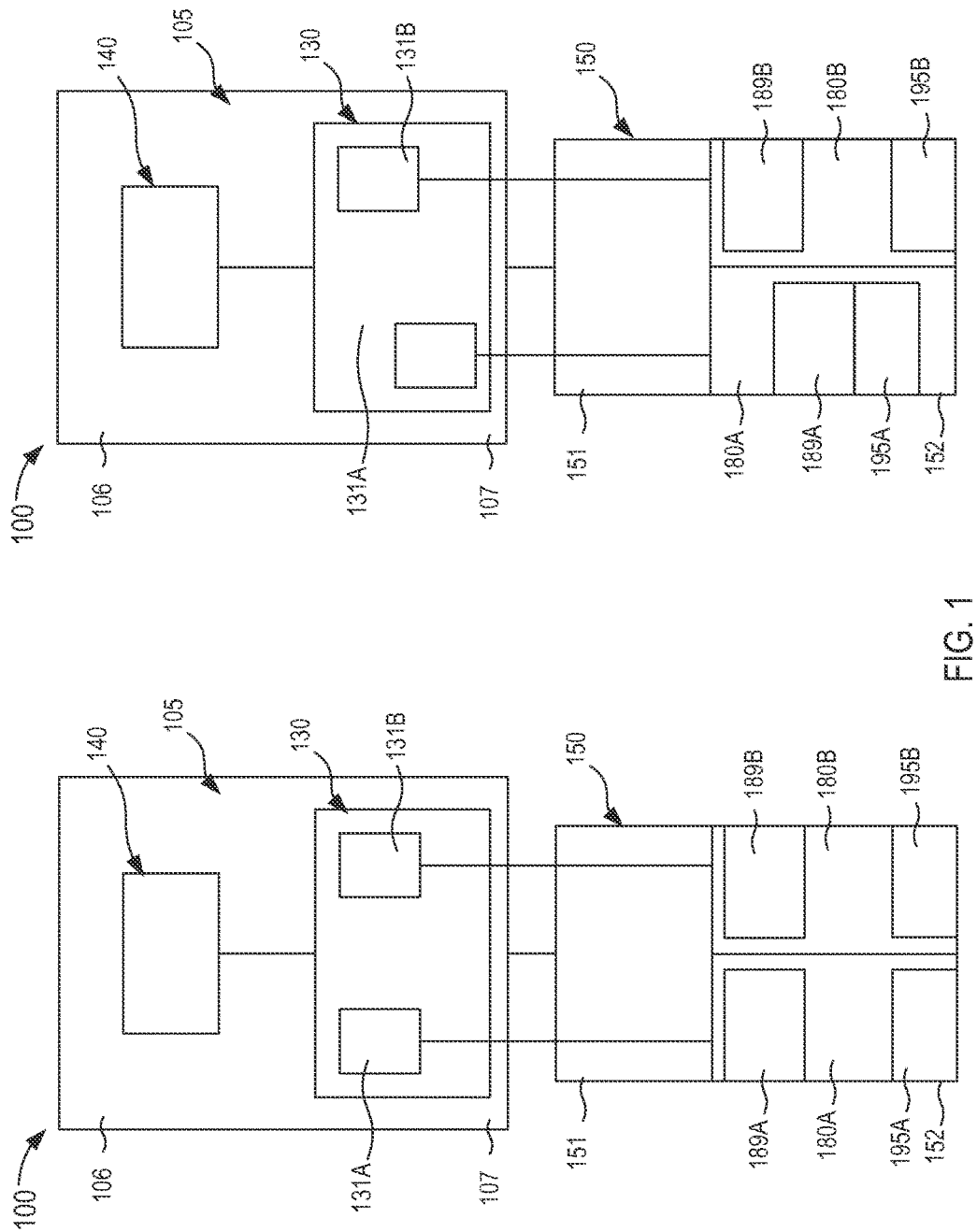

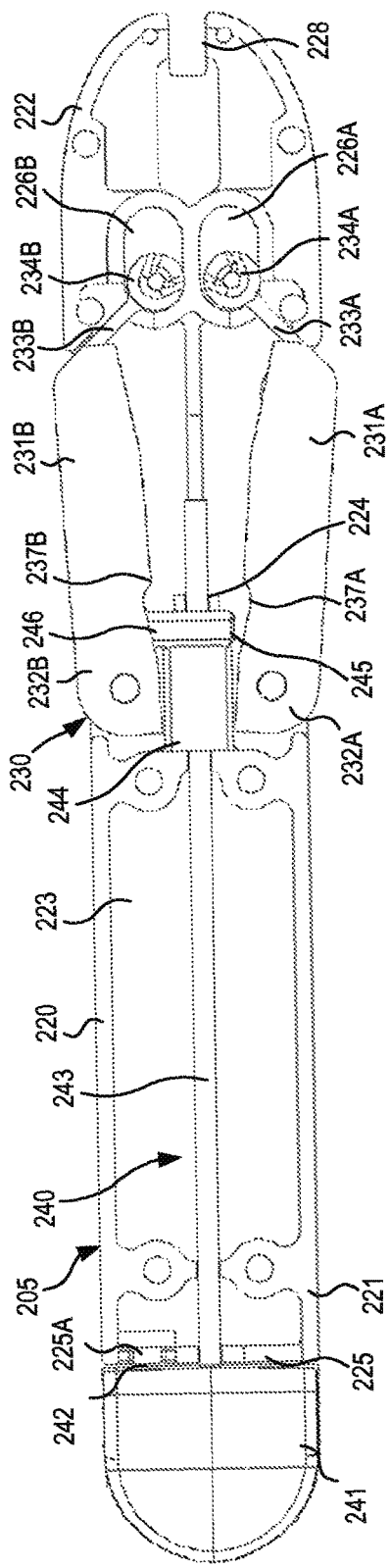
FIG. 8
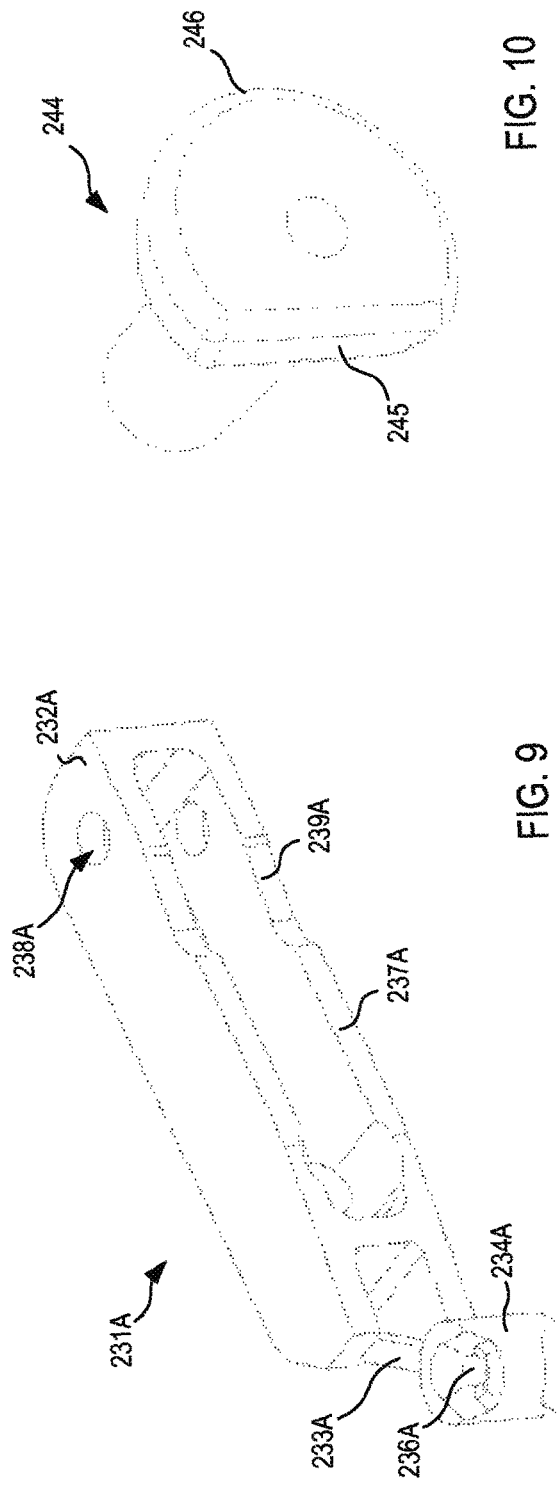
FIG. 10
FIG. 9

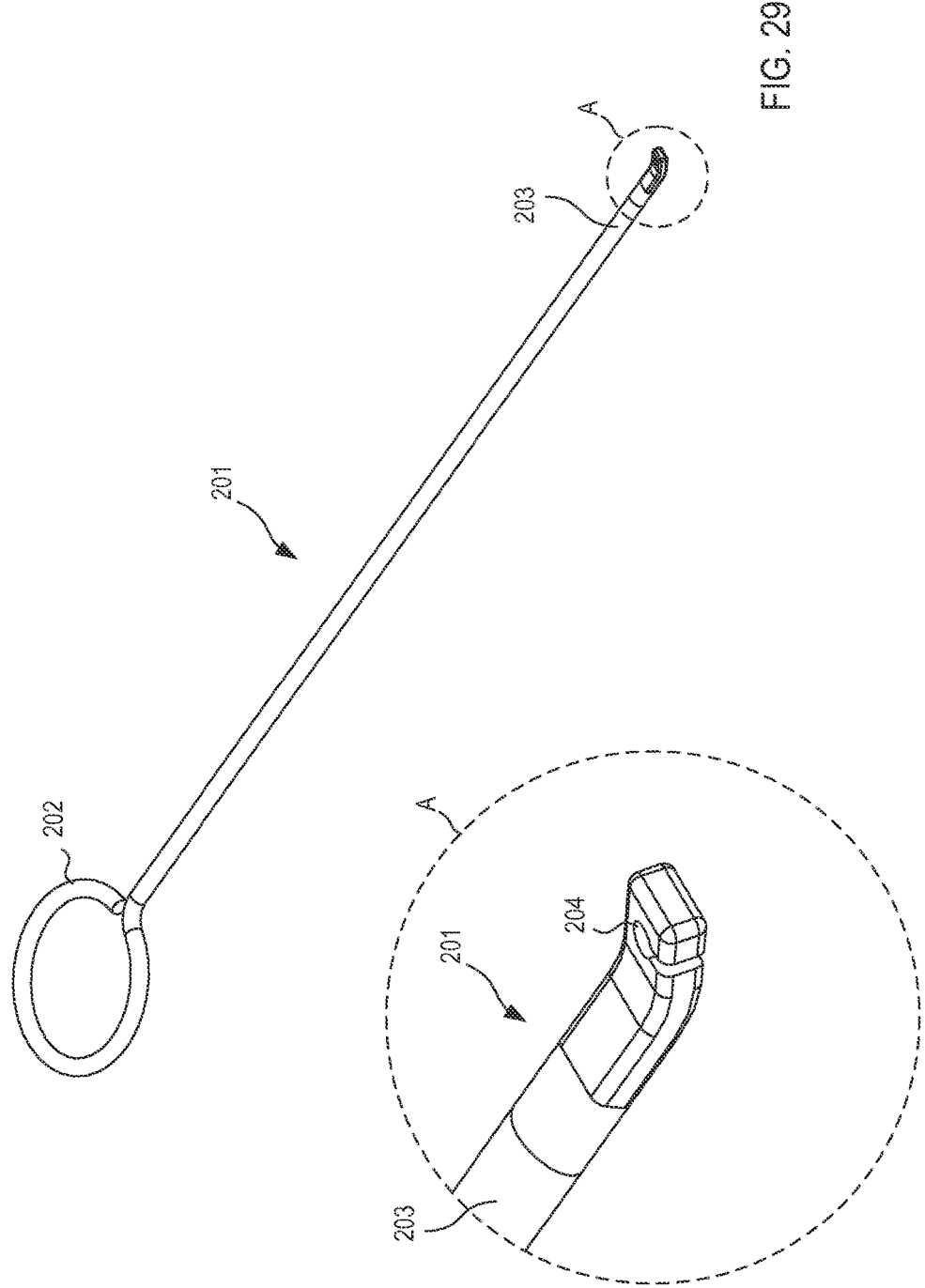

SUTURE REPAIR DEVICE

BACKGROUND

The present invention relates generally to surgery and the placement of sutures, and more particularly, to devices and methods for the suture repair of tissue, for example, tears of the dura mater that occur during spinal surgery.

Tears of the dura mater (durotomy) are a relatively common occurrence during spinal surgery. Incidences of durotomy can vary by procedure and can be an additional challenge during surgical repairs such as, for example, lumbar surgeries or the like. Moreover, it is desirable to form a substantially watertight closure of the dura mater to limit and/or avoid, for example, cerebrospinal fluid (CSF) leaks that can otherwise lead to patient complications including spinal headaches, meningitis, spinal fluid fistula, and epidural abscess.

Surgical closure techniques using sutures is a common approach to dural repair. In some instances, however, these techniques can be difficult to execute due to anatomic constraints, obstruction of visualization by CSF or blood, and the close proximity to the nerve rootlets. In some instances, these challenges can be further complicated when using minimally invasive techniques such as, for example, a tube retractor system. In some such instances, surgeons may choose not repair the durotomy or they may attempt to repair the durotomy using traditional suturing tools. Such tools and devices can be limited and, in some instances, lack maneuverability to avoid obstructions and/or to enable adequate passage of the needle and suture through the tissue. As a result, surgical repairs of the dura mater are often time consuming and expensive.

Thus, a need exists for methods and apparatus for the suture repair of tissue such as, for example, tears in the dura mater of the spine.

SUMMARY

The embodiments described herein are related to devices and methods for the suture repair of tissue, particularly tears of the dura mater that occur during spinal surgery. In some embodiments, an apparatus includes a handle, a cartridge, an actuator, and a lock. The handle has a proximal end portion and a distal end portion. The cartridge has a proximal end portion and a distal end portion. The proximal end portion of the cartridge is configured to be removably coupled to the distal end portion of the handle. The distal end portion of the cartridge includes a first needle assembly having a first needle and a first capture portion, and a second needle assembly having a second needle and a second capture portion. The actuator is movably coupled to the handle and has a first coupling portion and a second coupling portion, which are operably coupled to the first needle assembly and the second needle assembly, respectively, when the cartridge is coupled to the handle. The first coupling portion is configured to move relative to the handle in response to a first force to transition the first needle assembly from a first configuration in which the first capture portion is spaced apart from the first needle to a second configuration in which the first capture portion engages the first needle. The second coupling portion is configured to move relative to the handle in response to a second force to transition the second needle assembly from the first configuration in which the second capture portion is spaced apart from the second needle to a second configuration in which the second capture portion engages the second needle. The lock is operably coupled to the actuator and is configured to selectively limit movement of the first coupling portion and the second coupling portion.

BRIEF DESCRIPTION OF THE DRAWINGS

FIGS. 1 and 2 are schematic illustrations of a dural repair device in a first configuration and a second configuration, respectively, according to an embodiment.

FIG. 8 is a top view of a portion of the handle of FIG. 5 in a first configuration.

FIG. 9 is a perspective view of a first arm of an actuator included in the handle of FIG. 5.

FIG. 10 is a perspective view of a lock member of a lock included in the handle of FIG. 5.

FIG. 29 is a perspective view of a knot pusher according to an embodiment.

FIG. 30 is an enlarged perspective view of a portion of the knot pusher identified in FIG. 29 by the region A.

DETAILED DESCRIPTION

Figure 3:
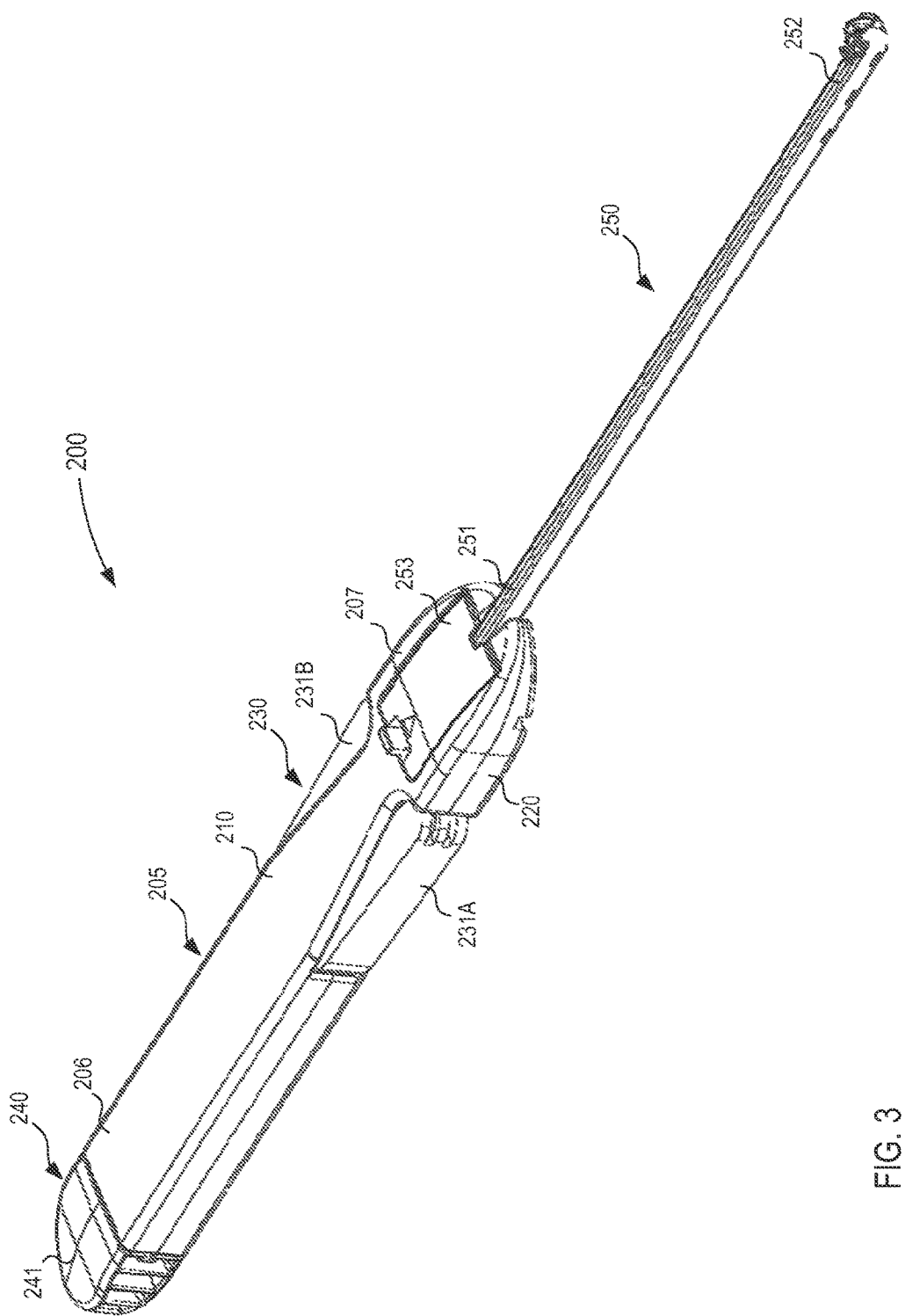
FIG. 3 is a perspective view of a dural repair device according to an embodiment.

In some embodiments, an apparatus includes a handle, a cartridge, an actuator, and a lock. The handle has a proximal end portion and a distal end portion. The cartridge has a proximal end portion and a distal end portion. The proximal end portion of the cartridge is configured to be removably coupled to the distal end portion of the handle. The distal end portion of the cartridge includes a first needle assembly having a first needle and a first capture portion, and a second needle assembly having a second needle and a second capture portion. The actuator is movably coupled to the handle and has a first coupling portion and a second coupling portion, which are operably coupled to the first needle assembly and the second needle assembly, respectively, when the cartridge is coupled to the handle. The first coupling portion is configured to move relative to the handle in response to a first force to transition the first needle assembly from a first configuration in which the first capture portion is spaced apart from the first needle to a second configuration in which the first capture portion engages the first needle. The second coupling portion is configured to move relative to the handle in response to a second force to transition the second needle assembly from the first configuration in which the second capture portion is spaced apart from the second needle to a second configuration in which the second capture portion engages the second needle. The lock is operably coupled to the actuator and is configured to selectively limit movement of the first coupling portion and the second coupling portion.

In some embodiments, an apparatus includes a handle, a cartridge, and an actuator. The handle has a proximal end portion and a distal end portion and defines a first channel and a second channel. The cartridge has a proximal end portion and a distal end portion. The proximal end portion of the cartridge is configured to be removably coupled to the distal end portion of the handle. The distal end portion of the cartridge includes a first needle assembly having a first needle and a first capture portion and a second needle assembly having a second needle and a second capture portion. The actuator is movably coupled to the handle. The actuator includes a first arm having a first deformable portion and a first coupling portion movably disposed in the first channel and operably coupled to the first needle assembly when the cartridge is coupled to the handle. The first deformable portion is configured to deform in response to a force exerted on the first arm to move the first coupling portion within the first channel such that movement of the first coupling portion from a first position to a second position transitions the first needle assembly from a first configuration, in which the first capture portion is spaced apart from the first needle, to a second configuration, in which the first capture portion is engaged with the first needle. The actuator including a second arm having a second deformable portion and a second coupling portion movably disposed in the second channel and operably coupled to the second needle assembly when the cartridge is coupled to the handle. The second deformable portion is configured to deform in response to a force exerted on the second arm to move the second coupling portion within the second channel such that movement of the second coupling portion transitions the second needle assembly from a first configuration, in which the second capture portion is spaced apart from the second needle, to a second configuration, in which the second capture portion is engaged with the second needle.

In some embodiments, a cartridge has a proximal end portion and a distal end portion. The proximal end portion of the cartridge is configured to be coupled to a handle. The distal end portion of the cartridge includes a needle assembly and defines a rotational axis. The needle assembly includes a needle and a capture portion. At least a portion of the needle assembly is configured to deform to rotate the needle and the capture portion about the rotational axis from a first configuration, in which the needle and the capture portion are spaced apart, to a second configuration, in which the capture portion engages the needle.

In some embodiments, a method of suturing a first target tissue of a patient to a second target tissue of the patient includes using a device with a handle having an actuator, and a cartridge configured to couple to the handle and including a first needle assembly having a first needle and a first capture portion and a second needle assembly having a second needle and a second capture portion. The method includes coupling the cartridge to the handle to operably couple the first needle assembly and the second needle assembly to the actuator. The first needle assembly is placed adjacent the first target tissue to position the first needle on a first side of the first target tissue and the first capture portion on a second side, opposite the first side, of the first target tissue. A first arm of the actuator is actuated to advance the first needle substantially through the first target tissue to be disposed on the second side of the first target tissue. The first capture portion is configured to engage the first needle when the first arm is actuated. The second needle assembly is placed adjacent the second target tissue to position the second needle on a first side of the second target tissue and the second capture portion on a second side of the second target tissue, opposite the first side of the second target tissue. A second arm of the actuator is actuated to advance the second needle substantially through the second target tissue to be disposed on the second side of the of the second target tissue. The second capture portion is configured to engage the second needle when the second arm is actuated.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to a direction closer to and away from, respectively, an operator of, for example, a medical device. Thus, for example, the end of the medical device contacting the patient's body would be the distal end of the medical device, while the end opposite the distal end would be the proximal end of the medical device.

As used herein, the terms "perpendicular" and "orthogonal" generally described a relationship between two geometric constructions (e.g., two lines, two planes, a line and a plane, or the like) in which the two geometric constructions are disposed at substantially 90°. For example, a line is said to be perpendicular to another line when the lines intersect at an angle substantially equal to 90°. Similarly, when a planar surface (e.g., a two dimensional surface) is said to be orthogonal to another planar surface, the planar surfaces are disposed at substantially 90° as the planar surfaces extend to infinity.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together (e.g., via a weld, an adhesive, or any suitable method).

As used herein, the term "stiffness" is related to an object's resistance to deflection, deformation, and/or displacement that is produced by an applied force, and is generally understood to be the opposite of the object's "flexibility." For example, a wall with greater stiffness is more resistant to deflection, deformation and/or displacement when exposed to a force than a wall having a lower stiffness. Similarly stated, an object having a higher stiffness can be characterized as being more rigid than an object having a lower stiffness. Stiffness can be characterized in terms of the amount of force applied to the object and the resulting distance through which an engagement portion of the object deflects, deforms, and/or displaces with respect to a coupling portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

Stiffness (and therefore, flexibility) is an extensive property of the object being described, and thus is dependent upon the material from which the object is formed as well as certain physical characteristics of the object (e.g., cross-sectional shape, length, boundary conditions, etc.). For example, the stiffness of an object can be increased or decreased by selectively including in the object a material having a desired modulus of elasticity, flexural modulus, and/or hardness. The modulus of elasticity, for example, is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be decreased, for example, by introducing into the object and/or constructing the object of a material having a relatively low modulus of elasticity.

In another example, the stiffness of the object can be increased or decreased by changing the flexural modulus of a material of which the object is constructed. Flexural modulus is used to describe the ratio of the applied stress on an object in flexure to the corresponding strain in the outermost portions of the object. The flexural modulus, rather than the modulus of elasticity, is used to characterize certain materials, such as plastics, which do not have substantially linear material properties over a range of conditions. An object with a first flexural modulus is less elastic and has a greater strain on the outermost portions of the object than an object with a second flexural modulus lower than the first flexural modulus. Thus, the stiffness of an object can be increased by including in the object a material having a high flexural modulus.

The stiffness of an object can also be increased or decreased by changing a physical characteristic of the object, such as the shape or cross-sectional area of the object. For example, an object having a length and a cross-sectional area may have a greater stiffness than an object having an identical length but a smaller cross-sectional area. As another example, the stiffness of an object can be reduced by including one or more stress concentration risers (or discontinuous boundaries) that cause deformation to occur under a lower stress and/or at a particular location of the object. Thus, the stiffness of the object can be decreased by decreasing and/or changing the shape of the object.

As used herein, the term "living hinge" can refer to a portion of a monolithically constructed object that can be deformed to allow for selective movement of the object. For example, a monolithically formed object can include two end portions, each of which have a first stiffness, separated by a deformable portion therebetween, which has a second stiffness that is less than the first stiffness. In response to an applied force, the deformable portion (i.e., the living hinge) can deform to allow for relative movement between the two end portions, thereby acting as a hinge. The stiffness of the deformable portion can be reduced, for example, by forming a discontinuity in one or more surfaces, reducing a thickness and/or cross-sectional area of the deformable portion, forming the deformable portion of a material with a lower modulus of elasticity or flexural modulus, and/or the like.

The embodiments described herein can be formed or constructed of one or more biocompatible materials. Examples of suitable biocompatible materials used to form the embodiments described herein include certain metals and/or polymers. Examples of suitable metals include pharmaceutical grade stainless steel, gold, titanium, nickel, iron, platinum, tin, chromium, copper, and/or alloys thereof. Suitable polymer materials may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly (butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof. While examples of suitable biocompatible materials are listed above, it should be understood that other materials, alloys, and/or copolymers may be used. Moreover, specific components of the embodiments described herein may be formed of a material, for example, based on its physical and/or mechanical properties. As one example, a component of the embodiments described herein configured to form a living hinge may be formed of a material, such as a polymer, having a relatively low stiffness.

Although the embodiments described herein specifically refer to suture repair of durotomy (e.g., of the spinal), it should be understood that the devices and methods described herein can be used for suture repair of any suitable tissue. For example, in some instances, the embodiments and methods described herein can be used in suture repair of any suitable target tissue when there are anatomic and/or other challenges to accessing, visualizing, and/or engaging the target tissue. In some instances, the embodiments and methods described herein can be used during, for example, minimally invasive surgeries. Thus, the embodiments and methods can increase effectiveness and/or efficiency of suture repair of a target tissue while reducing costs and surgical times.

FIGS. 1 and 2 are schematic illustrations of a dural repair device 100 in a first configuration and a second configuration, respectively, according to an embodiment. The dural repair device 100 can be any suitable shape, size, or configuration. For example, in some embodiments, the dural repair device 100 (also referred to herein as "repair device" or "device") can be used to suture torn or cut tissue during arthroscopic or other minimally invasive surgeries. By way of example, the repair device 100 can be used to suture tears in the dura mater during spinal surgery procedures or other similar procedures. In such procedures, anatomic structures can present challenges to accessing, during minimally invasive surgeries, a target tissue to be sutured (e.g., the dura). Thus, the repair device 100 can have a size, shape, and/or configuration that can increase the ease in accessing a target tissue as well as increase the ease in placing one or more sutures in the target tissue.

As shown in FIGS. 1 and 2, the device 100 includes a handle 105 and a cartridge 150. The handle 105 can be removably coupled to the cartridge 150 or fixedly coupled to the cartridge 150. For example, in some embodiments, the handle 105 can removably receive a portion of the cartridge 150 to be coupled thereto. In such embodiments, the cartridge 150 can be a disposable and/or single-use cartridge configured to place one or more sutures in a target tissue within the body, while the handle 105 can be, for example, a reusable device. In such embodiments, the cartridge 150 can be removably coupled to the handle 105, which in turn, remains physically and/or fluidically isolated from the body. Such a modular arrangement can, for example, increase the ease of use and minimize waste. Although described as being modular (e.g., the cartridge 150 being removably coupled to the handle 105), in other embodiments, the handle 105 and cartridge 150 can be integrally formed and/or otherwise assembled as a single device.

The handle 105 has a proximal end portion 106 and a distal end portion 107 and can be any suitable shape, size, and/or configuration. For example, in some embodiments, the handle 105 can have a size and/or shape that can allow for single-handed use. That is to say, when the device 100 is assembled (e.g., the cartridge 150 is coupled to the handle 105), a user such as a surgeon or the like can hold and/or manipulate the device 100 with one hand. As such, the handle 105 can be ergonomically designed to simplify, for example, the procedure of placing a suture in the dura mater, which in turn, can decrease surgery times and costs associated with a surgical procedure.

The handle 105 includes and/or otherwise at least partially houses an actuator 130 and a lock 140. For example, in some embodiments, the handle 105 defines an inner volume configured to movably receive at least a portion of the actuator 130 and at least a portion of the lock 140. Moreover, the handle 105 can include any suitable feature, protrusion, track, channel, groove, slot, etc. that can engage a portion of the actuator 130 and a portion of the lock 140 to define a range of motion of the actuator 130 and lock 140, respectively, relative to the handle 105, as described in further detail herein.

The actuator 130 includes a first arm 131A and a second arm 131B. The first arm 131A and the second arm 131B are movably coupled to the handle 105 such that an engagement portion of the first arm 131A and an engagement portion of the second arm 131B is disposed outside of the handle 105 and a coupling portion of the first arm 131A and a coupling portion of the second arm 131B is disposed inside the handle 105. For example, in some embodiments, the first arm 131A and the second arm 131B can be coupled to the handle 105 via a pin or mechanical fastener configured to allow the first arm 131A and the second arm 131B, respectively, to pivot or at least partially rotate relative to the handle 105. As described in further detail herein, the coupling portion of the first arm 131A and the coupling portion of the second arm 131B are configured to couple to a portion of the cartridge 150 when the cartridge 150 is coupled to the handle 105. In other words, the actuator 130 is coupled to a portion of the cartridge 150 when the cartridge 150 is coupled to the handle 105.

The coupling portion of the first arm 131A and the coupling portion of the second arm 131B can engage an inner surface of the handle 105 such that as when the first arm 131A and the second arm 131B, respectively, are rotated or pivoted relative to the handle 105, the coupling portion of the first arm 131A and the coupling portion of the second arm 131B, respectively, are moved in a substantially linear direction. For example, in some embodiments, the first arm 131A can include a deformable portion disposed between the engagement portion and the coupling portion of the first arm 131A that can bend, flex, and/or otherwise deform in response to a force exerted on the engagement portion (e.g., by a user). Thus, the deformable portion of the first arm 131A can be configured to transform a pivoting motion of the engagement portion of the first arm 131A into a translational motion of the coupling portion of the first arm 131A (e.g., in a proximal and distal direction). In other words, the deformable portion of the first arm 131A can be a living hinge or the like configured to allow for relative movement between the engagement portion and the coupling portion of the first arm 131A. The arrangement of the second arm 131B can be substantially similar to the arrangement of the first arm 131A; therefore, the second arm 131B can similarly include a deformable portion configured to allow relative movement between the engagement portion and the coupling portion of the second arm 131B. As such, a user can manipulate the engagement portion of the first arm 131A and/or the engagement portion of the second arm 131B to move the actuator 130 relative to the handle 105, which in turn, can transition the device 100 from the first configuration to the second configuration, as described in further detail herein.

The lock 140 can have any suitable arrangement configured to selectively limit movement of the first arm 131A or the second arm 131B relative to the handle 105. For example, the lock 140 can be disposed in a first configuration in which a portion of the lock 140 is in contact with, for example, a portion of the second arm 131B of the actuator 130 and not in contact with, for example, a portion of the first arm 131A of the actuator 130. Thus, with the portion of the lock 140 in contact with the second arm 131B, movement of the second arm 131B relative to the handle 105 is substantially prevented. Conversely, with the first arm 131A free from contact with the lock 140, the user can exert a force on the engagement portion of the first arm 131A to pivot the first arm 131A relative to the handle 105, which in turn, moves the coupling portion of the first arm 131A in a translational motion, for example, in a distal direction.

Although not shown in FIGS. 1 and 2, the lock 140 can include a selector or the like movably disposed outside of the handle. In some instances, a user can manipulate the handle 105 by rotating the selector relative to the handle 105 (e.g., about a longitudinal centerline defined by the handle 105, not shown in FIGS. 1 and 2). The rotation of the selector can result in a rotation of the lock 140 such that the portion of the lock 140 otherwise in contact with the second arm 131B is placed in contact with the first arm 131A. Thus, with the second arm 131B free from contact with the portion of the lock 140, the user can exert a force on the engagement portion of the second arm 131B to pivot the second arm 131B relative to the handle 105, which in turn, moves the coupling portion of the second arm 131B in a translational motion, for example, in the distal direction. Moreover, with the first arm 131A in contact with the portion of the lock 140, movement of the first arm 131A relative to the handle 105 is substantially prevented.

Although not shown in FIGS. 1 and 2, the handle 105 and/or the actuator 130 can include a bias member or the like configured to bias the first arm 131A and the second arm 131B relative to the handle 105. For example, in some embodiments, the actuator 130 can include a spring disposed between a portion of the first arm 131A and a portion of the second arm 131B. As such, the spring can exert a force to bias the first arm 131A and the second arm 131B in a predetermined position relative to the handle 105. In some embodiment, the arrangement of the actuator 130 can be such that when the first arm 131A and the second arm 131B are in the biased position, the coupling portion of the first arm 131A and the coupling portion of the second arm 131B are each in a proximal position. Therefore, when a user exerts a force to pivot, for example, the first arm 131A relative to the handle 105, the force can be sufficient to overcome a reaction force exerted by the bias member (e.g., spring), which in turn, moves the coupling portion of the first arm 131A in the distal direction.

The cartridge 150 of the device 100 has a proximal end portion 151 and a distal end portion 152 and can be any suitable shape, size, and/or configuration. For example, the cartridge 150 can have a relatively small, elongated shape and/or size that is suitable, for example, in minimally invasive surgical procedures, as described above. The proximal end portion 151 of the cartridge 150 is configured to removably or fixedly couple to the distal end portion 107 of the handle 105. In some embodiments, the proximal end portion 151 of the cartridge 150 and the distal end portion 107 of the handle 105 can collectively form a snap fit or the like configured to temporarily (e.g., removably) couple the cartridge 150 to the handle 105. In other embodiments, the cartridge 150 and the handle 105 can be preassembled to use. As described above, when the cartridge 150 is coupled to the handle 105, the cartridge 150 is operatively coupled to the actuator 130. For example, although not shown in FIGS. 1 and 2, the cartridge 150 can include a first push rod and/or connector configured to engage and/or otherwise couple to the coupling portion of the first arm 131A and a second push rod and/or connector configured to engage and/or otherwise couple to the coupling portion of the second arm 131B. Thus, the cartridge 150 can be operatively coupled to the actuator 130 when the cartridge 150 is coupled to the handle 105, as described in further detail herein.

The distal end portion 152 of the cartridge 150 can be any suitable configuration. In some embodiments, the distal end portion 152 of the cartridge 150 can have a size and/or shape configured to limit or substantially prevent the distal end portion 152 of the cartridge 150 from becoming stuck on and/or otherwise "snagging" undesired anatomic structures (e.g., nerves) as the distal end portion 152 of the cartridge 150 is moved through the body. For example, in some embodiments, the distal end portion 152 of the cartridge 150 can form a dogleg or the like. Alternatively, the distal end portion 152 can include a hook to the like configured to engage tissue (e.g., nerves) otherwise obstructing access to the target tissue.

The distal end portion 152 of the cartridge 150 includes a first needle assembly 180A and a second needle assembly 180B. The first needle assembly 180A and the second needle assembly 180B can be any suitable shape, size, or configuration. For example, as shown in FIGS. 1 and 2, the first needle assembly 180A includes a capture member 189A and a needle 195A and the second needle assembly 180B includes a capture member 189B and a needle 195B. The first needle assembly 180A and the second needle assembly 180B can be movably coupled to and/or otherwise movably disposed at the distal end portion 152 of the cartridge 150 (e.g., via a coupler a pin, a rod, an axle, a mechanical fastener, and/or the like). For example, in some embodiments, for example, the first needle assembly 180A and the second needle assembly 180B can be disposed about a pin or axle included in the distal end portion 152 of the cartridge 150 and configured such that the capture member 189A and the needle 195A of the first needle assembly and the capture member 189B and the needle 195B of the second needle assembly 180B can rotate about an axis defined by the pin or axle.

As described above with reference to the first arm 131A and the second arm 131B of the actuator 130, the first needle assembly 180A and the second needle assembly 180B each include one or more deformable portions configured to deform in response to an applied force. More specifically, the first needle assembly 180A can include a first deformable portion coupled to the capture member 189A and a second deformable portion coupled to the needle 195A (or portion of the first needle assembly 180A that is in turn coupled to the needle 195A). Similarly, the second needle assembly 180B can include a first deformable portion coupled to the capture member 189B and a second deformable portion coupled to the needle 195B (or portion of the first needle assembly 180B that is in turn coupled to the needle 195B). The deformable portions of the first needle assembly 180A and the second needle assembly 180B can each form and/or otherwise act as a living hinge configured to deform in response to an applied force (e.g., a force associated with the actuation of the actuator 130). For example, deformation of the deformable portions of the first needle assembly 180A and the second needle assembly 180B in response to an applied force can result in a rotation of the capture member 189A of the first needle assembly 180A and the capture member 189B of the second needle assembly 180B about the axis (e.g., defined by the pin or axle) in a first direction, and rotation of the needle 195A of the first needle assembly 180A and the needle 195B of the second needle assembly 180B about the axis in a second direction opposite the first direction. Thus, the rotation of capture member 189A and the needle 195A can transition the first needle assembly 180A from a first configuration (see e.g., FIG. 1), in which the capture member 189A is separated from the needle 195A, to a second configuration (see e.g., FIG. 2), in which the capture member 189A engages and at least temporarily captures the needle 195A, as described in further detail herein. Similarly, rotation of the capture member 189B and the needle 195B can transition the second needle assembly 180B from its first configuration to its second configuration.

Although not shown in FIGS. 1 and 2, the needle 195A of the first needle assembly 180A and the needle 195B of the second needle assembly 180B are coupled to a first end and a second end, respectively, of a suture. In other words, the distal end portion 152 of the cartridge 150 includes a single suture having a first end coupled to the needle 195A of the first needle assembly 180A and a second end coupled to the needle 195B of the second needle assembly 180B. In some embodiments, the cartridge 150 can include a housing, cover, pouch, and/or any other suitable retention means configured to house and/or retain the suture in a substantially fixed position as the cartridge 150 is placed in a desired position within the body. For example, the cartridge 150 can include a cover or the like extending between the proximal end portion 151 and the distal end portion 152 of the cartridge 150 configured to store a suture coupled to the needles 195A and 195B. As described in further detail herein, the device 100 can be placed in a desired position within the body and can be actuated to transition the first needle assembly 180A and/or the second needle assembly 180B from the first configuration to the second configuration and as such, advance the needles 195A and/or 195B and at least the ends of the suture through a target tissue. Thus, the device 100 can be used to place a suture in a target tissue, as described in further detail herein.

In some instances, the device 100 (i.e., the handle 105 and one or more cartridges 150) can be included in a substantially sterile packaging or the like. In use, a user, such as a surgeon, can remove the device 100 from the packaging and can manipulate the device 100 by coupling the proximal end portion 151 of the cartridge 150 to the distal end portion 107 of the handle 105. As described in detail above, coupling the cartridge 150 to the handle 105 operably couples the actuator 130 to the cartridge 150. In other embodiments, the cartridge 150 can be preassembled with the handle 105 (e.g., either fixedly coupled thereto or removably coupled during a manufacturing process or the like). With the cartridge 150 coupled to the handle 105, the user can manipulate the device 100 by inserting the cartridge into, for example, an incision in a patient and placing the distal end portion 152 of the cartridge 150 in a desired position relative to a target tissue. For example, in some embodiments, the device 100 can be used in a repair procedure in which a portion of a target tissue such as, for example, dura mater, on a first side of a tear therein is sutured to a portion of the target tissue on a second side of the tear. In such embodiments, the distal end portion 152 of the cartridge 150 can be placed on a distal side (e.g., relative to the device 100 or the user) of the portion of the dura mater on the first side of the tear.

Once in a desired position, the user can place and/or otherwise ensure that the lock 140 is in a configuration associated with preventing movement of the second arm 131B of the actuator 130. With the lock 140 in the desired configuration, the user can exert a force on, for example, the engagement portion of the first arm 131A to cause the first arm 131A to pivot relative to the handle 105. As described above, at least a portion of the force exerted by the user can deform the deformable portion (e.g., living hinge) of the first arm 131A such that as the engagement portion pivots relative to the handle 105, the coupling portion of the first arm 131A moves in a translational motion in the distal direction. The distal movement of the coupling portion, in turn, can move a push rod or the like (not shown in FIGS. 1 and 2) of the cartridge, a first end of which is in engaged with the coupling portion of the first arm 131A), in the distal direction. Although not shown in FIGS. 1 and 2, a second end of the push rod can be coupled to the first needle assembly 180A such that the distal movement of the push rod exerts a force on the first needle assembly 180A.

The force exerted on the first needle assembly 180A is sufficient to deform the deformable portions (described above) of the first needle assembly 180A. Thus, the force exerted by the user on the first arm 131A is operative to rotate the capture member 189A and the needle 195A of the first needle assembly 180A about the axis defined by the distal end portion 152 of the cartridge 150 (or a coupler coupled thereto), which in turn, transitions the first needle assembly 180A from the first configuration to the second configuration. Expanding further, the rotation of the needle 195A is such that the needle 195A is advanced through the target tissue such that at least a portion of the needle 195A is disposed on a proximal side of the target tissue (e.g., opposite the side of the target tissue when the first needle assembly 180A was in the first configuration), which places the device 100 in its second configuration, as shown in FIG. 2.

As described above, the capture member 189A and the needle 195A are placed in contact when the first needle assembly 180A is placed in its second configuration. More specifically, the capture member 189A can capture, retain, secure, and/or otherwise coupled to the needle 195A when the first needle assembly 180A is in the second configuration. In other words, the capture member 189A can be placed in contact with a portion of the needle 195A when the first needle assembly 180A is placed in the second configuration such that the needle 195A is retained in a substantially fixed position relative to the capture member 189A. For example, in some embodiments, the capture member 189A can have and/or can include a geometry, plate, contour, etc. configured to secure and/or capture the needle 195A when placed in contact therewith.

With the first needle assembly 180A in its second configuration, the user can remove the force exerted on the first arm 131A and can pull the device 100 (at least slightly) in the proximal direction. The arrangement of the first arm 131A and the first needle assembly 180A is such that when the force otherwise resulting in the deformation of the deformable portions of the first arm 131A and the first needle assembly 180A, respectively, the deformable portions transition from their deformed state back to a substantially undeformed state. That is to say, while the deformable portions are configured to deform, the deformable portions are nonetheless biased toward an undeformed state. Said yet another way, the force exerted on the engagement portion of the first arm 131A elastically deforms the deformable portions of the first arm 131A and the first needle assembly 180A and thus, when the force is removed, the deformable portions return to a substantially undeformed state. Thus, as described above, the deformable portions are living hinges configured to deform to result in relative movement between portions of a monolithically formed component (i.e., the first arm 131A and the first needle assembly 180A). Moreover, by removing the force from the first arm 131A, the first needle assembly 180A transitions from its second configuration toward its first configuration; however, with the needle 195A captured and/or retained by the capture member 189A the needle 195A rotates concurrently and in the same direction with the capture member 189A. In this manner, the needle 195A is further advanced through the target tissue such that the end of the needle 195A that is coupled to the suture is advanced through the target tissue.

With a portion of the suture extending through the target tissue, the user can manipulate the device 100 to place the distal end portion 152 of the cartridge 150 on a distal side of the portion of the target tissue on the second side of the tear. Once in a desired position, the user can place and/or otherwise ensure that the lock 140 is in a configuration associated with preventing movement of the first arm 131A of the actuator 130 while not inhibiting movement of the second arm 131B of the actuator 130. With the lock 140 in the desired configuration, the user can exert a force on, for example, the engagement portion of the second arm 131B to cause the second arm 131B to pivot relative to the handle 105. As described above with reference to the first arm 131A and the first needle assembly 180A, the force exerted on the second arm 131B is sufficient to place the second needle assembly 180B in its second configuration. Thus, the needle 195B of the second needle assembly 180B is advanced through the target tissue such that at least a portion of the needle 195B is disposed on a proximal side of the target tissue, as described above with reference to the first needle assembly 180A.

With the second needle assembly 180B in its second configuration (e.g., with the capture member 189B in contact with the needle 195B, as described above with reference to the first needle assembly 180A), the user can remove the force exerted on the second arm 131B and can pull the device 100 (at least slightly) in the proximal direction. Thus, the second arm 131B and the second needle assembly 180B transition from their second configurations toward their first configurations; however, with the needle 195B captured and/or retained by the capture member 189B the needle 195B rotates concurrently and in the same direction with the capture member 189B. In this manner, the needle 195B is further advanced through the target tissue such that the end of the needle 195B that is coupled to the suture is advanced through the target tissue. With one end of the suture extending through the target tissue on the first side of the tear and the opposite end of the suture extending through the target tissue on the second side of the tear, the suture can be pulled to close at least a portion of the tear in the target tissue and once that portion is substantially closed, the user can tie a knot in the suture, thereby suturing the tear in the target tissue. Although not shown in FIGS. 1 and 2, in some embodiments, the user can use a knot pusher (e.g., included in the substantially sterile packaging within which the device 100 was disposed) to push or cinch the knot down to the target tissue.

In some instances, a tear in a target tissue can call for more than one suture. In such instances, the user can, after placing the first suture, decouple the cartridge 150 from the handle 105 and can couple an unused cartridge 150 to the handle 105. Thus, the user can perform substantially the same procedure as described above to place any suitable number of sutures within a target tissue. In some embodiments, the substantially sterile packaging can include multiple cartridges 150 (e.g., two, three, four, or more). In other embodiments, the handle 105 and the cartridge 150 can be discarded after placing the first suture and a new handle 105 and cartridge 150 can be used in substantially the same procedure to place any number of subsequent sutures. In still other embodiments, the cartridge 150 can be configured to place any number of sutures or, for example, a running suture.

FIGS. 3-28 illustrate a dural repair device 200 according to another embodiment. The dural repair device 200 can be any suitable shape, size, or configuration. For example, in some embodiments, the dural repair device 200 (also referred to herein as "repair device" or "device") can be used to suture torn or cut tissue during arthroscopic or other minimally invasive surgeries. By way of example, the repair device 200 can be used to suture tears in the dura mater during spinal surgery procedures or other similar procedures. In such procedures, anatomic structures can present challenges, during minimally invasive surgeries, to accessing a target tissue to be sutured (e.g., the dura). Thus, the repair device 200 can have a size, shape, and/or configuration that can increase the ease in accessing a target tissue as well as increase the ease in placing one or more sutures in the target tissue.

Figure 4:
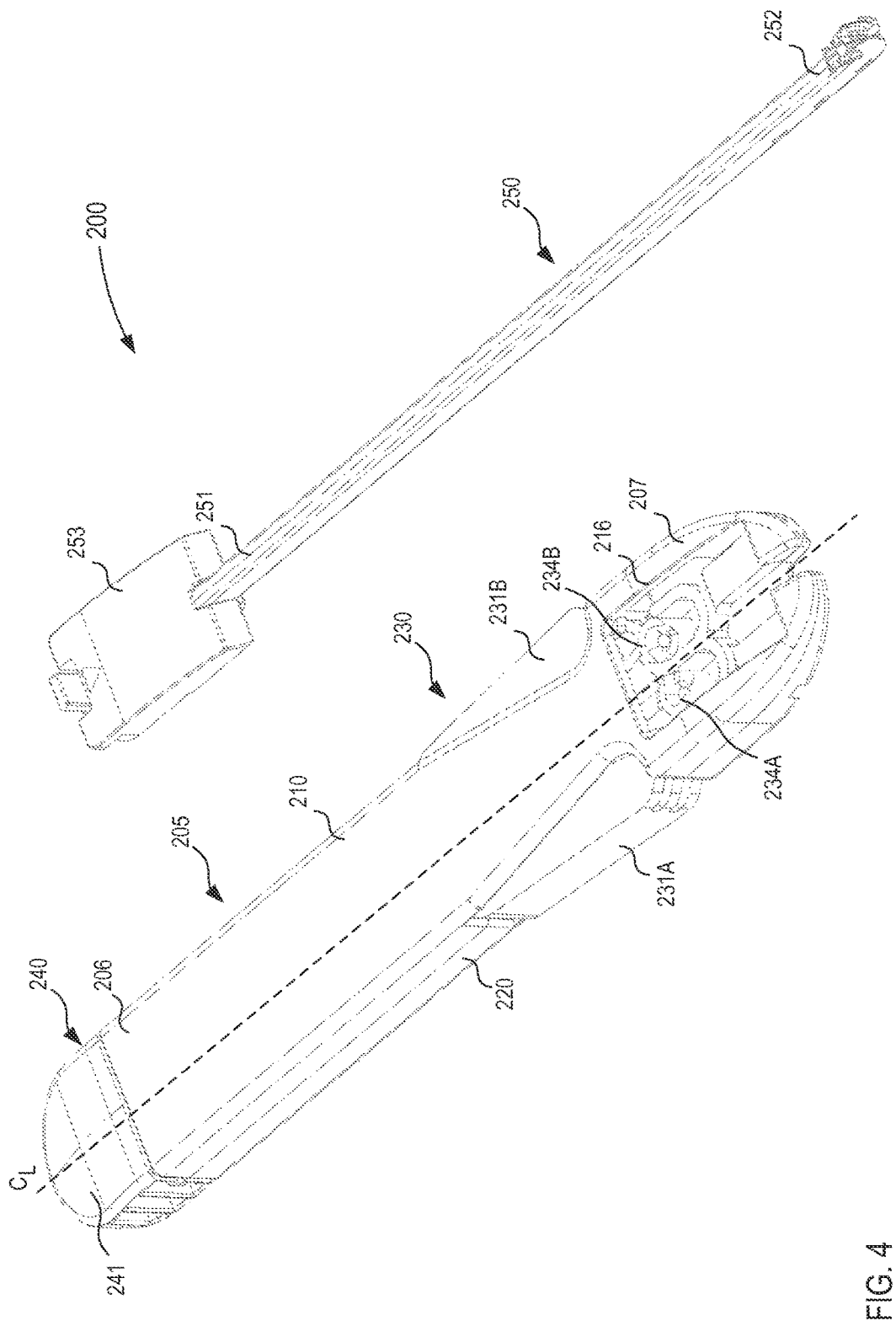
FIG. 4 is a partially exploded perspective view of the dural repair device of FIG. 3.

As shown in FIGS. 3 and 4, the device 200 includes a handle 205 and a cartridge 250. In this embodiment, the cartridge 250 is configured to be removably coupled to the handle 205. In this manner, the cartridge 250 can be a disposable and/or single-use cartridge configured to place one or more sutures in a target tissue within the body, while the handle 205 can be, for example, a reusable device. Thus, after placing at least one suture, the cartridge 250 can be removed from the handle 205 and discarded, while a second, unused cartridge 250 is coupled to the handle 205 to place an additional suture. Although described as being modular (e.g., the cartridge 250 being removably coupled to the handle 205), in other embodiments, the handle 205 and cartridge 250 can be integrally formed and/or otherwise assembled as a single device.

The handle 205 has a proximal end portion 206 and a distal end portion 207 and can be any suitable shape, size, and/or configuration. For example, in some embodiments, the handle 205 can have a size and/or shape that can allow for single-handed use. That is to say, when the device 200 is assembled (e.g., the cartridge 250 is coupled to the handle 205), a user such as a surgeon or the like can hold and/or manipulate the device 200 with one hand. As such, the handle 205 can be ergonomically designed to simplify, for example, the procedure of placing a suture in the dura mater, which in turn, can decrease surgery times and costs associated with a surgical procedure. Moreover, the handle 205 can be formed of any suitable material or combination of materials. For example, in some embodiments, the handle 205 can be formed of a biocompatible material such as those described herein. In some embodiments, the handle 205 can include a surface finish and/or can be formed of a material that is substantially non-slip.

Figure 5:
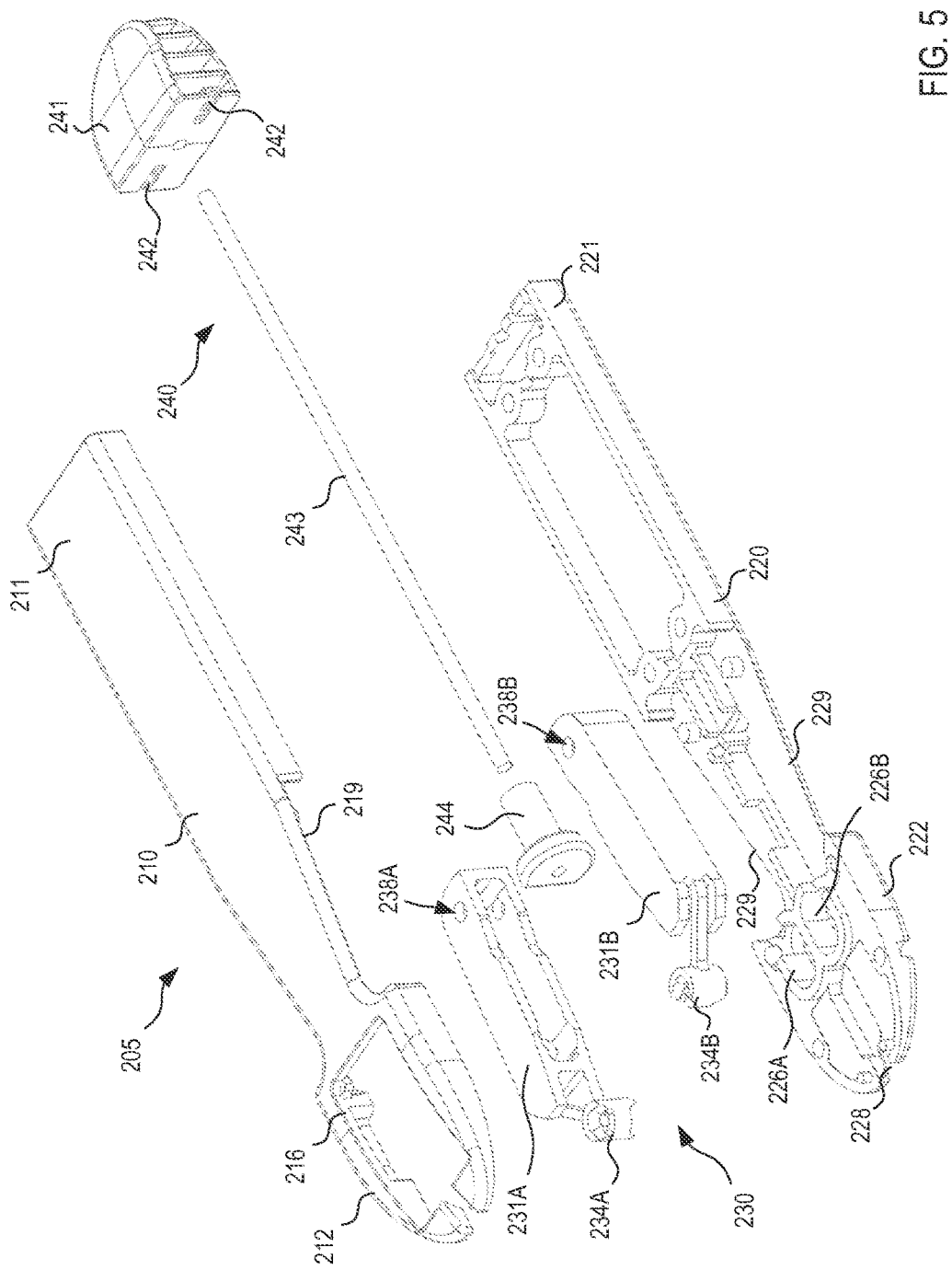
FIG. 5 is an exploded perspective view of a handle included in the dural repair device of FIG. 3.
Figure 6:
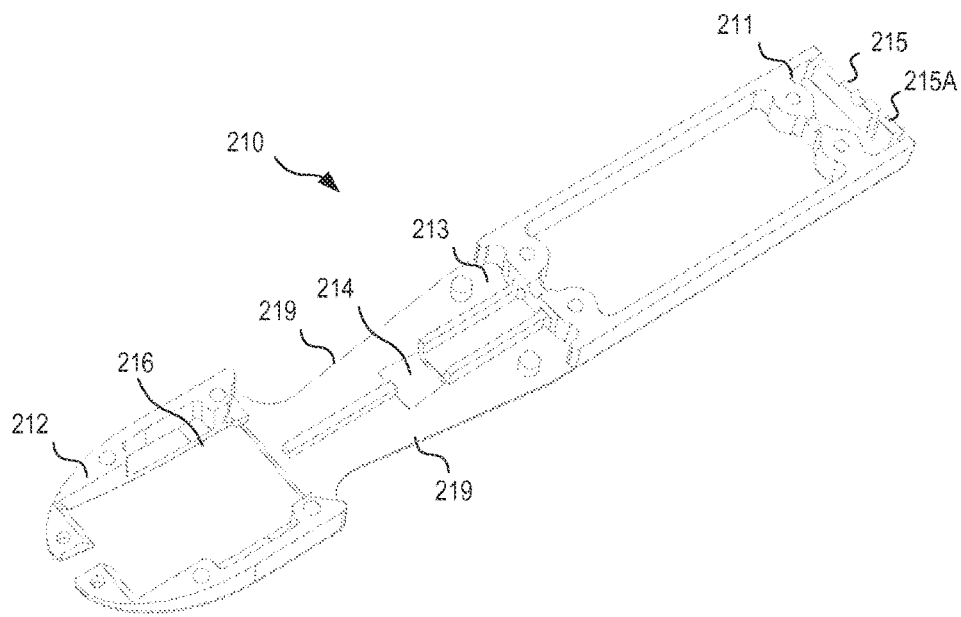
FIGS. 6 and 7 are perspective views of a first member and second member, respectively, of the handle illustrated in FIG. 5.

As shown in FIG. 5, the handle 205 includes and/or otherwise at least partially houses an actuator 230 and a lock 240. For example, the handle 205 includes a first member 210 and a second member 220 that can be coupled to collectively define an inner volume configured to movably receive at least a portion of the actuator 230 and at least a portion of the lock 240. As shown in FIG. 6, the first member 210 of the handle 205 has a proximal end portion 211 and a distal end portion 212 and an inner surface 213. Additionally, the first member 210 defines a cartridge opening 216 configured to receive a portion of the cartridge 250 and a set of actuator openings 219 each of which is configured to receive a different portion of the actuator 230.

The proximal end portion 211 of the first member 210 includes a proximal wall 215 having a selector tab 215A. The selector tab 215A is configured to be in contact with a portion of the lock 240 to selectively retain the portion of the lock 240 in a fixed position, at least temporarily, as described in further detail herein. The distal end portion 212 of the first member 210 defines the cartridge opening 216. The cartridge opening 216 is configured to receive the portion of the cartridge 250 when the cartridge 250 is coupled to the handle 205. More specifically, the distal end portion 212 of the first member 210 can define the cartridge opening 216 such that at least a portion of the cartridge 250 engages a portion of the inner surface 213 of the first member 210, as described in further detail herein.

The inner surface 213 can have any suitable feature, protrusion, post, opening, recess, or the like configured to accommodate any suitable portion of the handle 205, actuator 230, and/or lock 240. For example, the inner surface 213 defines the recess 214 configured to movably receive a portion of the lock 240. In other words, the recess 214 can be configured to limit and/or substantially prevent interference between the inner surface 213 and the first member 210 of the handle 205 that may otherwise inhibit movement of the lock 240 within the handle 205. Moreover, the inner surface 213 can define any suitable post, opening, and/or mating surface configured to engage and/or receive an associated feature on an inner surface 223 of the second member 220 when the first member 210 is coupled to the second member 220. Similarly, the inner surface can include any suitable post, protrusion, coupler, and/or feature configured to movably couple a portion the actuator 230 to the handle 205, as described in further detail herein.

Figure 7:
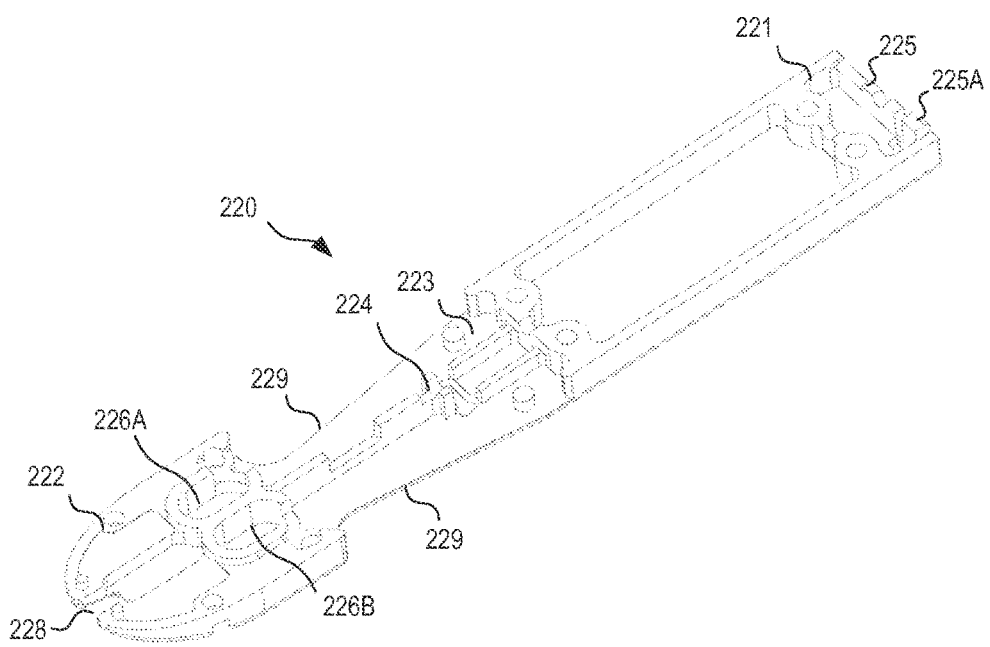

As shown in FIG. 7, the second member 220 of the handle 205 has a proximal end portion 221 and a distal end portion 222 and an inner surface 223. Additionally, the second member 220 defines a set of actuator openings 229 each of which is configured to receive a different portion of the actuator 230. As described above with reference to the first member 210, the proximal end portion 221 of the second member 220 includes a proximal wall 225 having a selector tab 225A. The selector tab 225A is configured to be in contact with a portion of the lock 240 to selectively retain the portion of the lock 240 in a fixed position, at least temporarily, as described in further detail herein. The distal end portion 222 of the second member 220 defines a slot 228 configured to receive a portion of the cartridge 250 when the cartridge 250 is coupled to the handle 205.

The inner surface 223 can have any suitable feature, protrusion, post, opening, recess, or the like configured to accommodate any suitable portion of the handle 205, actuator 230, and/or lock 240. For example, the inner surface 223 includes a lock rod support 224 configured to movably support a portion of the lock 240. In addition, the inner surface 223 includes and/or defines a first channel 226A and a second channel 226B each of which is configured to receive a portion of the actuator 230. As shown in FIG. 7, the first channel 226A and the second channel 226B are substantially parallel and extend along a longitudinal centerline $C_L$ (see e.g., FIG. 4) of the handle 205. In other words, the channels 226A and 226B extend between a proximal position along the longitudinal centerline $C_L$ and a distal position along the longitudinal centerline $C_L$. In this manner, each of the channels 226A and 226B can receive a portion of the actuator 230 and can define a range of motion associated with that portion of the actuator 230, as described in further detail herein. Moreover, the inner surface 223 can define any suitable post, opening, and/or mating surface configured to engage and/or receive an associated feature on an inner surface 213 of the first member 210 when the second member 220 is coupled to the first member 210. Similarly, the inner surface 223 can include any suitable post, protrusion, coupler, and/or feature configured to movably couple a portion the actuator 230 to the handle 205, as described in further detail herein.

As shown in FIGS. 8 and 9, at least a portion of the actuator 230 of the device 200 is movably disposed within the handle 205. The actuator 230 includes a first arm 231A and a second arm 231B each of which is movably coupled to the first member 210 and the second member 220 of the handle 205. For example, the first arm 231A defines an opening 238A configured to receive a pin, post, and/or any other suitable protrusion extending from the inner surface 213 of the first member 210 and/or the inner surface 223 of the second member 220. Similarly, the second arm 231B defines an opening 238B configured to receive a pin, post, and/or any other suitable protrusion extending from the inner surface 213 of the first member 210 and/or the inner surface 223 of the second member 220. This arrangement, for example, can be such that when a force is exerted on the first arm 231A or the second arm 231B, the first arm 231A or the second arm 231B, respectively, pivot about an axis defined by the openings 238A and 238B, respectively, relative to the handle 205, as described in further detail herein.

The first arm 231A and the second arm 231B are substantially similar and are coupled to the handle 205 in a substantially similar manner but in opposite orientations, as shown in FIG. 8. The first arm 231A and the second arm 231B can be formed of any suitable material or materials such as those described. More specifically, the first arm 231A and the second arm 231B can be formed from a relatively flexible material such as a plastic or the like. As described in further detail herein, by forming the first arm 231A and the second arm 231B of the relatively flexible material can be such that a portion of the first arm 231A and a portion of the second arm 231B bend, flex, bow, and/or otherwise deform in response to an applied force associated with actuation of the first arm 231 and the second arm 231B.

The first arm 231A includes an engagement portion 232A, a deformable portion 233A, a coupling portion 234A, and an inner surface 237A. Similarly, the second arm 231B includes an engagement portion 232B, a deformable portion 233B, a coupling portion 234B, and an inner surface 237B. With the arms 231A and 231B being substantially similar, a discussion of the first arm 231A with reference to FIG. 9 is intended to apply to both the first arm 231A and the second arm 231B. As shown, the engagement portion 232A defines the opening 238A and thus, the engagement portion 232A movably couples the first arm 231A to the handle 231A. Moreover, the engagement portion 232A extends through the actuator opening 219 of the first member 210 and the actuator opening 229 of the second member 220 of the handle 205. In this manner, a user can exert a force on the engagement portion 232A to pivot the first arm 231A relative to the handle 205 from a first configuration to a second configuration. In other words, the user can exert a force on the engagement portion 232A to actuate the first arm 231A. Similarly, the user can exert a force on the engagement portion 232B to actuate the second arm 231B and to transition the second arm 231B from a first configuration to a second configuration.

The coupling portion 234A of the first arm 231A (and the coupling portion 234B of the second arm 231B) can be any suitable shape, size, and/or configuration. For example, in this embodiment, the coupling portion 234A is substantially cylindrical and defines an opening 236A configured to receive a portion of the cartridge 250, as described in further detail herein. The coupling portion 234A is movably disposed in the first channel 226A by the second member 220 of the handle 205, as shown in FIG. 8. Similarly, the coupling portion 234B of the second arm 231B is movably disposed in the second channel 226B of the second member 220 of the handle 205. As described in further detail herein, the coupling portion 234A of the first arm 231A and the coupling portion 234B of the second arm 231B are configured to move in a translational motion within the channels 226A and 226B, respectively, in response to the actuation of the first arm 231A and the second arm 231B, respectively. In other words, the coupling portions 234A and 234B are configured to move within the channels 226A and 226B, respectively, between a proximal position and a distal position when the first arm 231A and the second arm 231B pivot relative to the handle 205, as described in further detail herein.

The deformable portion 233A of the first arm 234A (and the deformable portion 233B of the second arm 234B) can be any suitable shape, size, and/or configuration. As shown in FIGS. 8 and 9, for example, the deformable portion 233A is a relatively thin extension that couples the engagement portion 232A to the coupling portion 234A. More specifically, the deformable portion 233A is a relatively flexible portion of the first arm 231A that is configured to deform in response to an applied force. For example, as described above, the first arm 231A is formed of a relatively flexible material such as a plastic or the like. Thus, the first arm 231A has a stiffness that is dependent on the material properties of the constituent material (e.g., the flexural modulus) as well as the physical properties of the first arm 231A such as cross-sectional shape and/or area. As shown in FIG. 9, the deformable portion 233A of the first arm 231A has a significantly smaller cross-sectional shape than, for example, the engagement portion 232A and/or the coupling portion 234A. Thus, the stiffness (or flexibility) of the deformable portion 233A is less than a stiffness of the engagement portion 232A and/or the coupling portion 234A.

Figure 11:
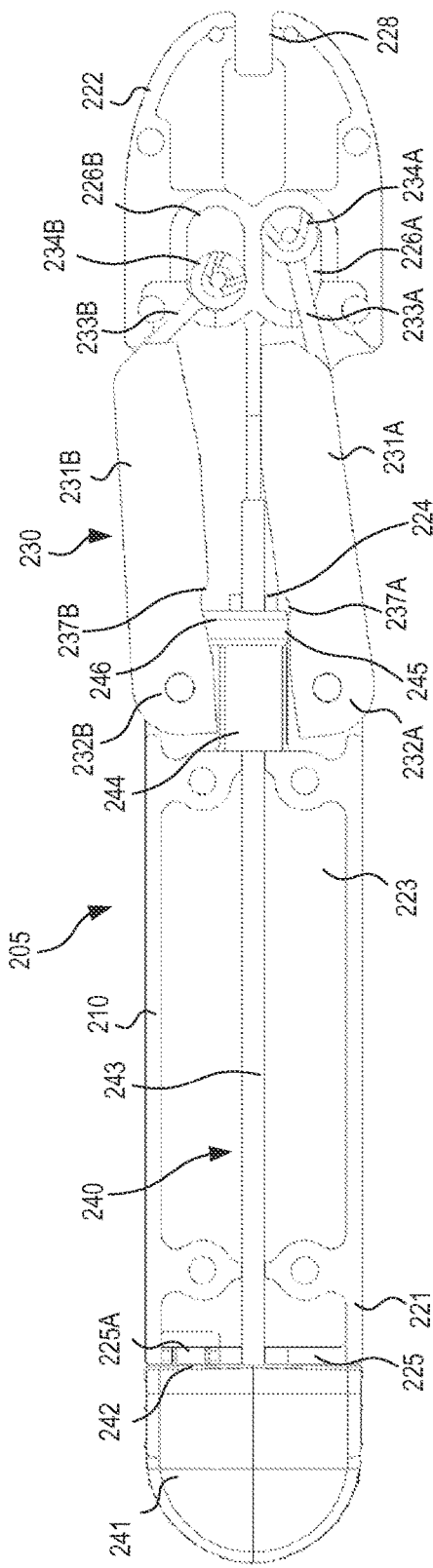
FIGS. 11 and 12 are each a top view of the portion of the handle of FIG. 8 in a second configuration and a third configuration, respectively.

The arrangement of the deformable portion 233A is such that a force sufficient to deform the deformable portion 233A may not be sufficient to substantially deform the engagement portion 232A and/or the coupling portion 234A of the first arm 231A. For example, with the engagement portion 232A coupled to the handle 205 for pivoting motion and with the channel 226A defining a translational range of motion of the coupling portion 234A in a direction parallel to the longitudinal axis $C_L$, the application of a force exerted by the user on the engagement portion 232A results in a bending, flexing, bowing, and/or deflection of the deformable portion 233A. In other words, the deformable portion 233A of the first arm 231A can deform and/or deflect in response to a force exerted on the engagement portion 232A to transform a pivoting motion of the engagement portion 232A into a translational motion of the coupling portion 234A within the channel 226A of the second member 220 of the housing (e.g., in the proximal or distal direction). Said another way, the deformable portion 233A of the first arm 231A can be a living hinge or the like configured to allow for relative movement between the engagement portion 232A and the coupling portion 234A in response to an actuation of the first arm 231A (e.g., the application of a force on the engagement portion 232A). Thus, the deformable portion 233A deforms and/or deflects in response to an actuation force exerted on the engagement portion 232A to transition the first arm 231A from its first configuration (FIG. 8) to its second configuration (FIG. 11).

Figure 12:
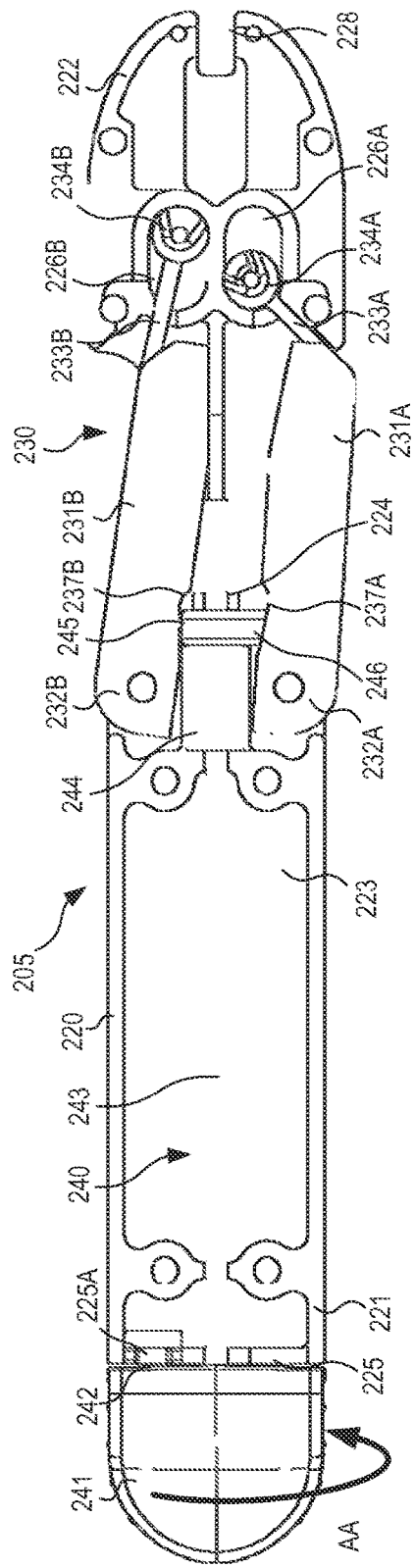

The arrangement of the deformable portion 233B of the second arm 231B is substantially similar to the arrangement of the deformable portion 233A of first arm 231A; therefore, actuation of the second arm 231B similarly results in deformation and/or deflection of the deformable portion 233B operative to transform the pivoting motion of the engagement portion 232B into the translational motion of the coupling portion 234B. In other words, the deformable portion 233B deforms and/or deflects in response to an actuation force exerted on the engagement portion 232B to transition the second arm 231B from its first configuration (FIGS. 8 and 11) to its second configuration (FIG. 12). As such, a user can manipulate the engagement portion 232A of the first arm 231A and/or the engagement portion 232B of the second arm 231B to move the actuator 230 relative to the handle 205, which in turn, can transition the device 200 from the first configuration to the second configuration, as described in further detail herein.

The inner surface 237A of the first arm 231B (and the inner surface 237B of the second arm 231B) can have any suitable contour and/or can include or define any suitable feature. As described in further detail herein, a portion of the inner surface 237A of the first arm 237A (and a portion of the inner surface 237B of the second arm 237B) is configured to selectively engage a portion of the lock 240 to selectively limit movement of the first arm 231A (or the second arm 231B) relative to the handle 205. Moreover, the first arm 231A can be and/or can form a substantially hollow shell (e.g., can have relatively thin walls that define a volume, as shown in FIG. 9). Although not shown herein, in some embodiments, this arrangement can accommodate a bias member, which can be disposed within the substantially hollow shell of the first arm 231A and the second arm 231B. For example, in some embodiments, the actuator 230 includes a spring or the like having a first end that is disposed within a portion of the hollow shell formed by the first arm 231A and a second end that is disposed within a portion of the hollow shell formed by the second arm 231B. In such embodiments, the spring (or other bias member) can exert an equal and opposite force on the arms 231A and 231B that is operative in biasing the arms 231A and 231B in their first configuration. Therefore, a force exerted on the first arm 231A or the second arm 231B sufficient to pivot the engagement portions 232A or 232B overcomes a reaction force exerted by the spring (or other bias member).

Although described, for example, as a linear spring disposed between the first arm 231A and the second arm 231B, in other embodiments, the actuator 230 can include a first torsional spring or the like configured to engage a surface of the engagement portion 232A of the first arm 231A as the engagement portion 232A pivots relative to the handle 205. Similarly, the actuator 230 can include a second torsion spring or the like configured to engagement a surface of the engagement portion 232B of the second arm 231B as the engagement portion 232B pivots relative to the handle 205. In still other embodiments, the actuator 230 can include any other suitable bias member and/or arrangement of one or more bias members configured to bias the first arm 231A and the second arm 231B in their first configuration until an actuation force or the like is exerted on the engagement portions 232A and 232B, respectively.

As shown in FIGS. 10-12, the lock 240 of the device 200 can have any suitable shape, size, and/or configuration. The lock 240 is at least partially disposed in the handle 205 and is configured to selectively limit movement of the first arm 231A or the second arm 231B relative to the handle 205 (FIGS. 11 and 12). The lock 240 includes a selector 241, a lock rod 243, and a lock member 244. The lock member 244 includes a first portion 245 and a second portion 246 (see e.g., FIG. 10) and is movably disposed within the handle 205 (see e.g., FIGS. 11 and 12). The first portion 245 of the lock member 244 forms and/or includes a substantially flat or linear peripheral surface, while the second portion 246 forms and/or includes a substantially curvilinear or semi-circular peripheral surface. As described in further detail herein, the lock member 244 can be moved within the handle 205 to place the second portion 246 in contact with the inner surface 237A or 237B of the first arm 231A or the second arm 231B, respectively.

As shown in FIGS. 11 and 12, at least a portion of the lock rod 243 is movably disposed within the handle 205 such that a first end is coupled to the lock member 244. Moreover, the lock rod 243 is disposed within the handle 205 such that at least a portion of the lock rod 243 (e.g., the first end) is support by the lock rod support 224 of the second member 220 of the handle 205. A second end, opposite the first end, of the lock rod 243 extends through the proximal wall 215 of the first member 210 and the proximal wall 225 of the second member 220 of the handle 205 to couple to the selector 241. The selector 241 is disposed outside of the handle 205 and is coupled to the second end of the lock rod 243. More specifically, the selector 241 includes a set of notches 242 (e.g., grooves, slots, recesses, and/or the like, see e.g., FIG. 5) and is disposed relative to the handle 205 such that the selector tab 215A of the first member 210 is disposed within a first notch 242 and the selector tab 225B of the second member 220 is disposed within a second notch 242. As such, a surface of the selector 241 defining the notches 242 and the selector tabs 215A and 215B can define a friction fit or the like configured to at least temporarily retain the selector 241 in a substantially fixed position relative to the handle 205 until a force sufficient to overcome the frictional forces is exerted on the selector 241. Moreover, in some embodiments, the selector tabs 215 and 225 of the handle 205 and/or the surface of the selector 241 defining the notches 242 (or both) produce a haptic or audible indication (e.g., a click or the like) associated with placing the selector 241 in a desired position.

The selector 241 can be manipulated by a user to transition the lock 240 from a first configuration to a second configuration. For example, the user can rotate the selector 241 relative to the handle 205, which in turn, rotates the lock rod 243 and the lock member 244 within the handle 205, as indicated by the arrow AA in FIG. 12. In other words, the user can rotate the selector 241 to transition the lock 240 between a first configuration (FIG. 11) and a second configuration (FIG. 12).

As shown in FIG. 11, for example, when the lock 240 is in its first configuration, the lock member 244 is oriented within the handle 205 such that the second portion 246 (e.g., having the rounded or curvilinear peripheral surface) of the lock member 244 is in contact with the inner surface 237B of the second arm 231B, while the first portion 245 of the lock member 244 (e.g., having the substantially linear peripheral surface) is not in contact with the inner surface 237A of the first arm 231A. Therefore, with the lock rod 243 supported by the lock rod support 224 of the second member 220 of the handle 205 and with the second portion 246 of the lock member 244 in contact with the inner surface 237B of the second arm 231B, pivoting motion of the engagement portion 232B of the second arm 231B is limited and/or substantially prevented. Conversely, with the first portion 245 of the lock member 244 adjacent to the first arm 231A, the engagement portion 232A of the first arm 231A can pivot relative to the handle 205 in response to an actuation force exerted on the engagement portion 232A. In other words, the lack of contact between the inner surface 237A of the first arm 231A and the first portion 245 of the lock member 244 when the lock is in its first configuration is such that the lock member 244 does not inhibit or restrict pivoting motion of the engagement portion 232A of the first arm 231A. Moreover, as shown in FIG. 11, when the engagement portion 232A of the first arm 231A pivots relative to the handle 205, the deformable portion 233A can bend, flex, deform, and/or deflect such that the pivoting motion of the engagement portion 232A (e.g., in response to an applied force) results in a translational motion of the coupling portion 234A within the first channel 226A from a proximal position to a distal position, as described above.

As shown in FIG. 12, when the user rotates the selector 241 (e.g., in the direction of the arrow AA) relative to the handle 205 to place the lock 240 in its second configuration, the lock member 244 is rotated relative to the actuator 230 such that the second portion 246 of the lock member 244 is in contact with the inner surface 237A of the first arm 231A and the first portion 245 of the lock member 244 is disposed adjacent to but not in contact with the inner surface 237B of the second arm 231B. Thus, as described above with reference to the first arm 231A, when is force exerted to pivot the engagement portion 232B of the first arm 231B relative to the handle 205, the deformable portion 233B bends, flexes, deforms, and/or deflects such that the pivoting motion of the engagement portion 232B results in a translational motion of the coupling portion 234B within the second channel 226B from a proximal position to a distal position, as shown in FIG. 12).

Figure 13:
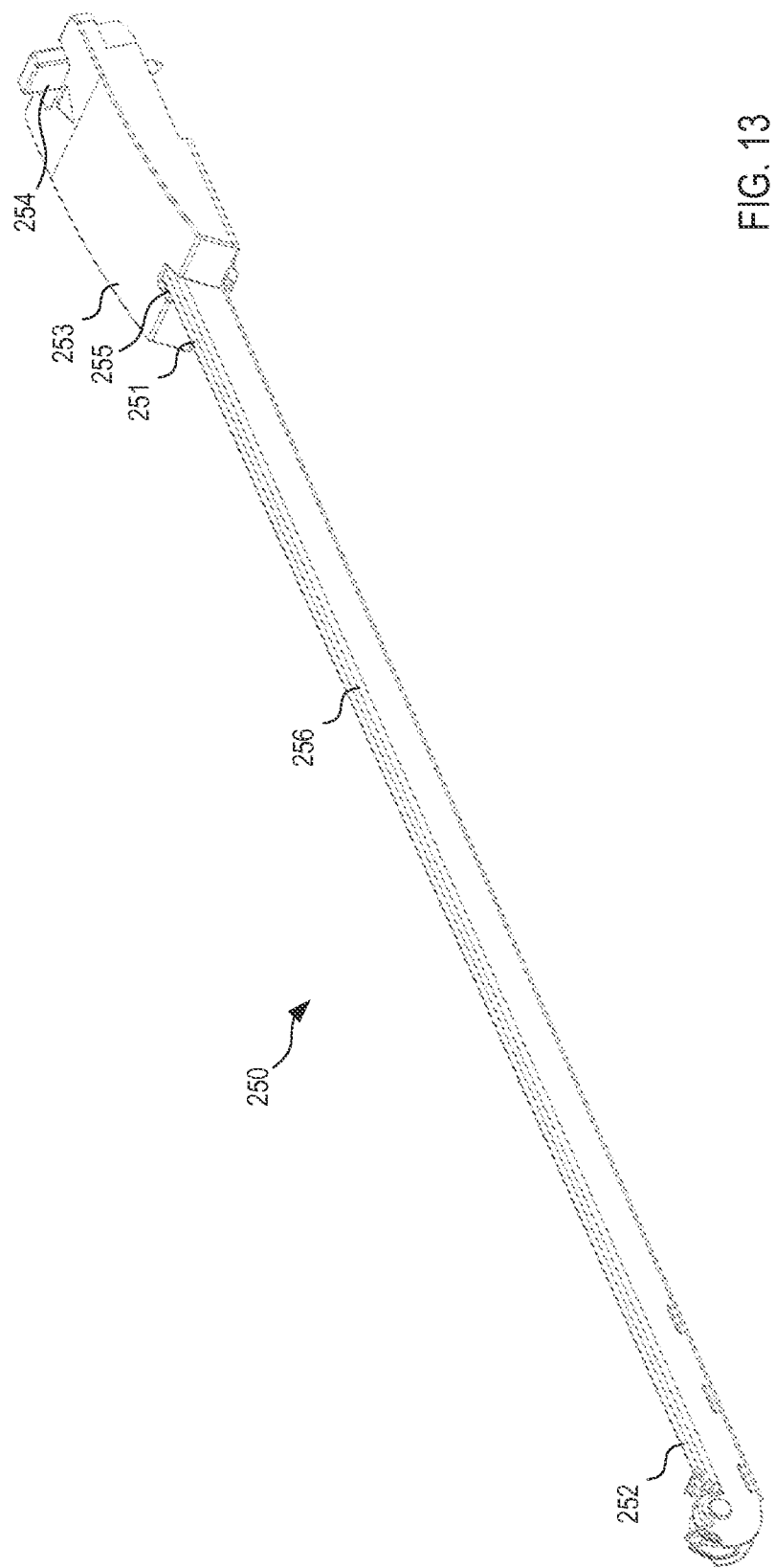
FIG. 13 is a perspective view of a cartridge included in the dural repair device of FIG. 3.
Figure 14:
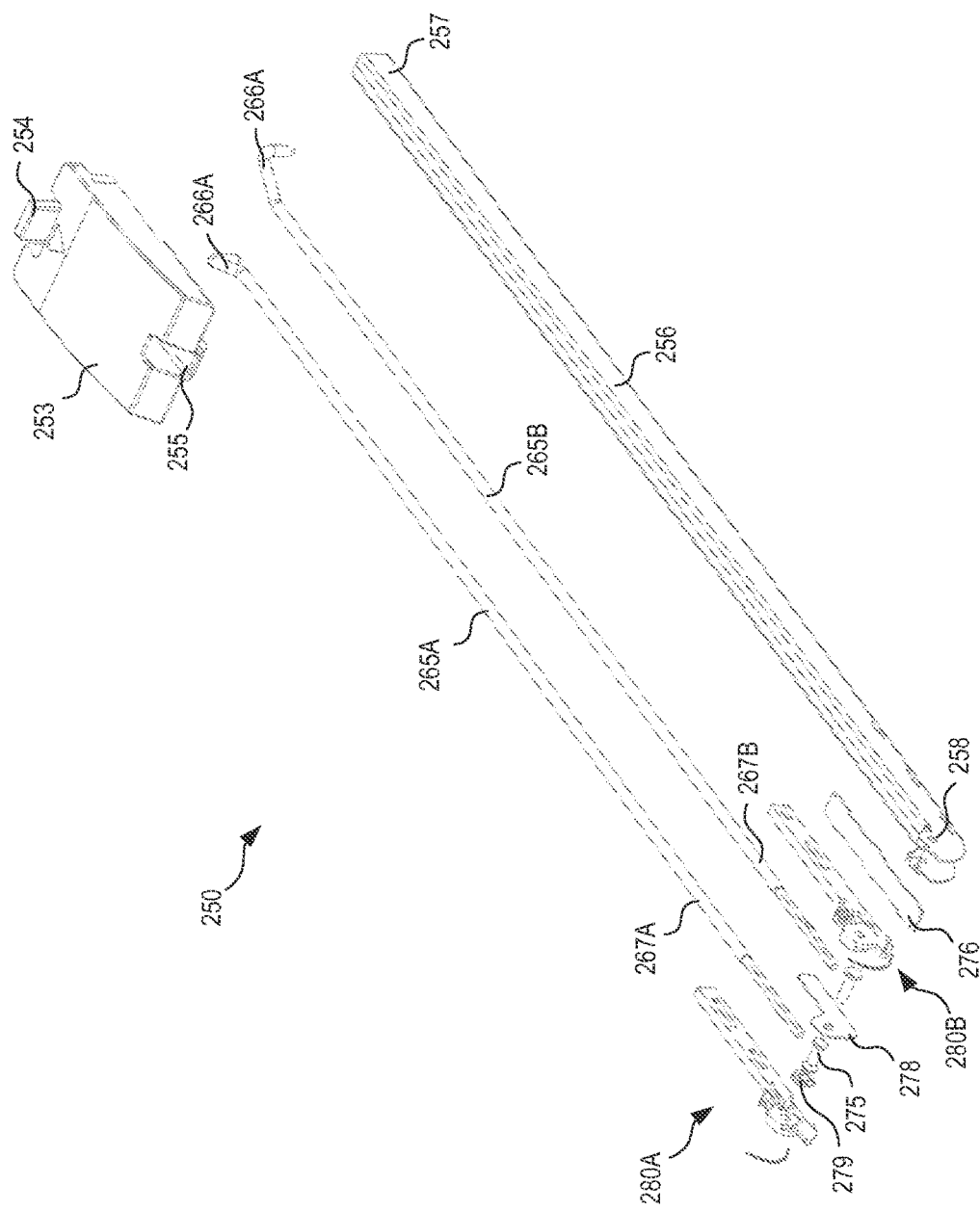
FIG. 14 is an exploded perspective view of the cartridge illustrated in FIG. 13.

As shown in FIGS. 13-28, the cartridge 250 of the device 200 is configured to removably couple to the handle 205 and has a relatively small, elongated shape and/or size that is suitable, for example, in minimally invasive surgical procedures, as described above. The cartridge 250 has a proximal end portion 251 and a distal end portion 252. As shown in FIGS. 13 and 14, the cartridge 250 includes an elongate shaft 256 having a proximal end portion 257 and a distal end portion 258 and defining an inner volume 259. The elongate shaft 256 extends from the proximal end portion 251 of the cartridge 250 to the distal end portion 252 of the cartridge 250 and is configured to receive and/or at least partially house a first needle assembly 280A, a second needle assembly 280B, a first push rod 265A coupled to the first needle assembly 260A, a second push rod 265B coupled to the second needle assembly 280B, a pin 275, a separation plate 276, a central plate 278, and one or more biased washers 279, as described in further detail herein.

Figure 15:
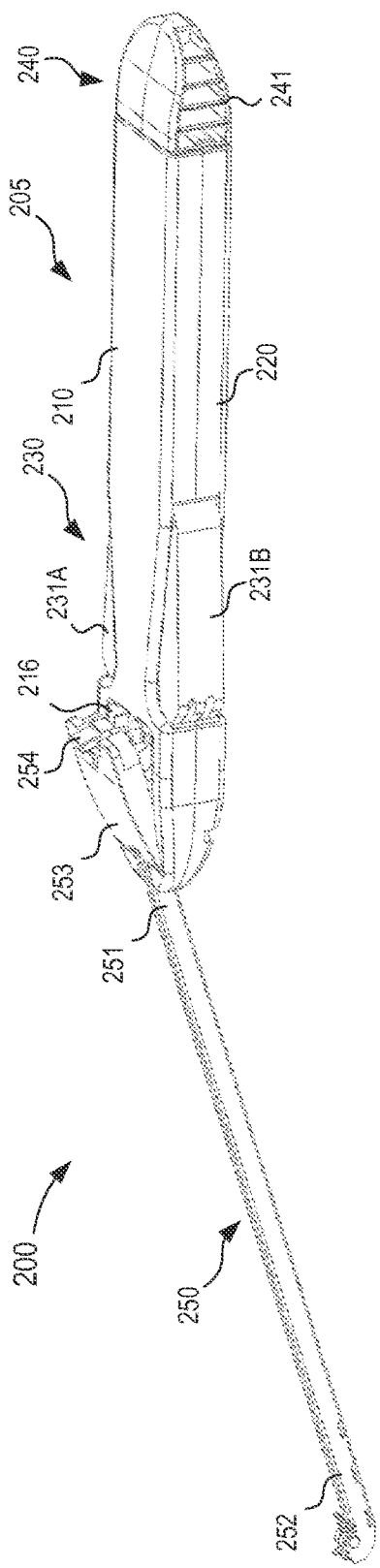
FIG. 15 is a side perspective view of the dural repair device of FIG. 3, illustrating the cartridge being coupled to the handle.
Figure 16:
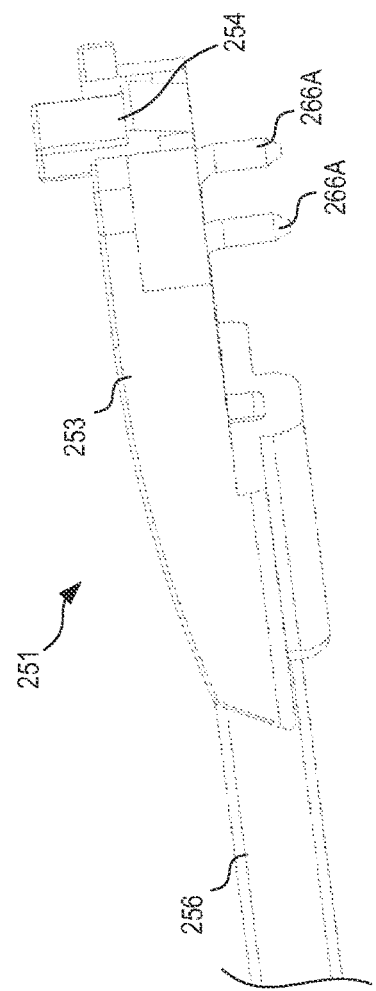
FIG. 16 is an enlarged perspective view of a proximal end portion of the cartridge illustrated in FIG. 13.

The proximal end portion 251 of the cartridge 250 includes an attachment member 253 configured to removably couple the cartridge 250 to the handle 205, as shown in FIGS. 15 and 16. More specifically, the attachment member 253 can be at least partially inserted into the cartridge opening 216 defined by the first member 210 of the handle 205 (FIG. 15). The attachment member 253 includes a tab 254 configured to engage the inner surface 213 of the first member 210 of the handle 205 when the attachment member 253 is positioned within the cartridge opening 216. The tab 254, for example, can include a flange, rib, protrusion, and/or the like configured to collectively form a friction fit or a snap fit operative to at least temporarily coupling the cartridge 250 to the handle 205.

Figure 17:
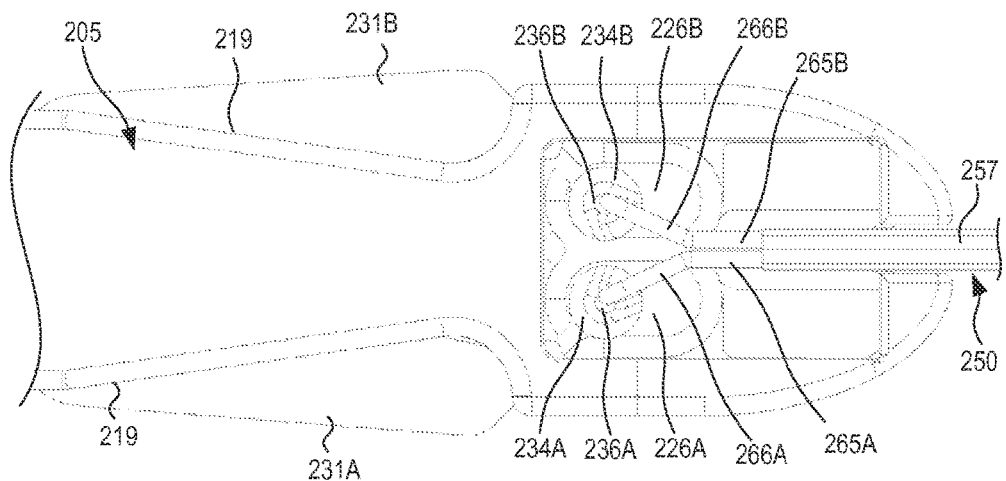
FIG. 17 is an enlarged top view of the proximal end portion of the cartridge illustrated in FIG. 16 coupled to the distal end portion of the handle illustrated, for example, in FIG. 8.

As described above, when the cartridge 250 is coupled to the handle 205, the cartridge 250 is operatively coupled to the actuator 230. For example, as shown in FIGS. 16 and 17, a proximal end portion 266A of the first push rod 265A and a proximal end portion 266B of the second push rod 265B extend through the proximal end portion 257 of the elongate shaft. Each proximal end portion 266A and 266B of the push rods 265A and 265B forms a dogleg or bend, as shown in FIG. 16. In this manner, when the cartridge 250 is positioned within the cartridge opening (FIG. 15), the proximal end portion 266A of the first push rod 265A can be aligned with and inserted into the opening 236A defined by the coupling portion 234A of the first arm 231A of the actuator 230, as shown in FIG. 17. Similarly, the proximal end portion 266B of the second push rod 265B can be aligned with and inserted into the opening 236B defined by the coupling portion 234B of the second arm 231B of the actuator 230. Thus, with the first push rod 265A coupled to the first needle assembly 280A and the second push rod 265B coupled to the second needle assembly 280B, coupling the cartridge 250 to the handle 205 operatively couples the first arm 231A of the actuator 230 to the first needle assembly 280A and the second arm 231B of the actuator to the second needle assembly 280B. As such, actuating the first arm 231A (e.g., applying a force to the engagement portion 232A of the first arm 231A) results in the first needle assembly 280A being transitioned from a first configuration to a second configuration and actuating the second arm 231B results in the second needle assembly 280B being transitioned from a first configuration to a second configuration, as described in further detail herein.

Figure 18:
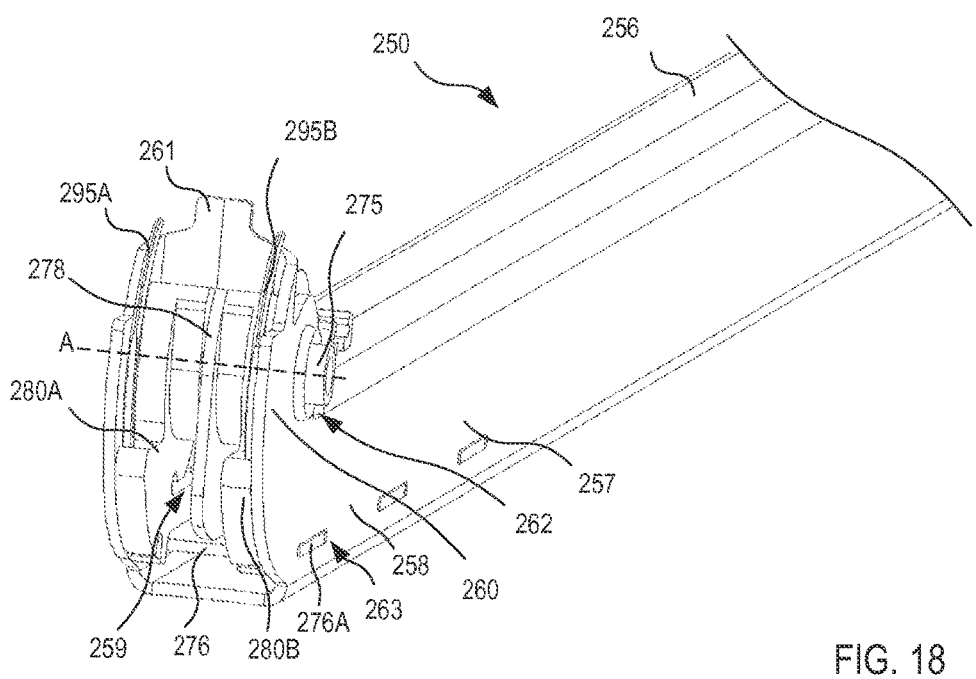
FIG. 18 is a front perspective view of a distal end portion of the cartridge illustrated in FIG. 13.
Figure 19:
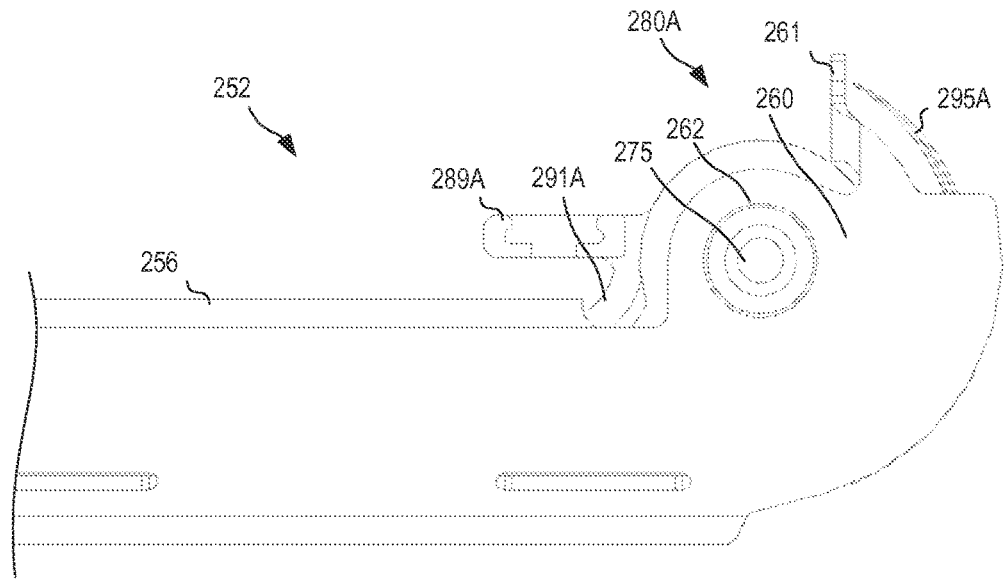
FIG. 19 is a side view of a distal end portion of the cartridge illustrated in FIG. 13.

The distal end portion 252 of the cartridge 250 includes the first needle assembly 280A, the second needle assembly 280B, the pin 275, the separation plate 276, the central plate 278, and the one or more biased washers 279, as shown in FIGS. 18 and 19. In addition, the elongate shaft 256 extends toward the distal end portion 252 of the cartridge 250 to at least partially cover or enclose the distal end portion 252 of the cartridge 250. The distal end portion 258 of the elongate shaft 256 (or the distal end portion 252 of the cartridge 250) can be any suitable shape, size, or configuration. For example, the distal end portion 258 of the elongate shaft 256 can have a size and/or shape configured to limit or substantially prevent the distal end portion 258 of the elongate shaft 256 (or the cartridge 250) from becoming stuck on and/or otherwise "snagging" undesired anatomic structures (e.g., nerves) as the distal end portion 252 of the cartridge 250 is moved through the body.

For example, as shown in FIGS. 18 and 19, the distal end portion 258 of the elongate shaft 256 forms and/or includes a doglegged region 260 extending from a surface of the elongate shaft 256. The doglegged region 260 includes a distal tip 261 and defines an opening(s) 262 extending through a width of the elongate shaft 256. The opening(s) 262 is/are configured to receive the pin 275, which extends substantially through the opening(s) 262 (not shown). In this manner, the pin 262 fixedly couples to the doglegged region 260 and defines an axis A, as shown in FIG. 18. Moreover, the first needle assembly 280A, the second needle assembly 280B, the central plate 289, and the one or more biased washers are disposed about the pin 262 and substantially within the inner volume 259 defined by the elongate shaft 256. As described in further detail herein, this arrangement is such that at least a portion of the first needle assembly 280A and at least a portion of the second needle assembly 280B can rotate about the axis A defined by the pin 262 to transition between at least the first configuration and the second configuration. The distal tip 261 of the doglegged region 260 is configured to limit a rotation of the first needle assembly 280A and the second needle assembly 280B about the axis A. In addition, the distal tip 261 can be used, for example, as a hook or a guard to facilitate the navigation of the distal end portion 252 of the cartridge 250 to the desired position relative to the target tissue, which, for example, can reduce a risk of damage to sensitive anatomy such as nerves.

While the distal tip 261 is shown, for example, in FIG. 18 as having a given shape and/or configuration, in other embodiments, the distal tip 261 can have any suitable shape, size, and/or configuration. For example, in some embodiments, the distal tip 261 can include an extension and/or can otherwise extend a greater distance from the doglegged region 260 relative to the distal tip 261 shown in FIG. 18. Moreover, in some embodiments, the distal tip 261 can be disposed at and/or otherwise extend at any suitable angle. For example, while the distal tip 261 is shown in FIG. 18 as being substantially perpendicular to the elongate shaft 256, in other embodiments, the distal tip 261 can be disposed at angle other than a perpendicular angle relative to the elongate shaft 256. In some embodiments, for example, at least a portion of the distal tip 261 can extend from the doglegged portion 260 at any suitable angle in the distal direction, and/or the like. In other embodiments, the arrangement and/or angle of the distal tip 261 can be adjustable (e.g., a user can exert a force on the distal tip 261 to bend, flex, move, and/or otherwise reconfigure the distal tip 261).

Referring back to FIG. 14, the separation plate 276 and the central plate 278 can be any suitable shape, size, and/or configuration. For example, the separation plate 276 can have a size (e.g., length) based at least in part on a size (e.g., length) associated with the first needle assembly 280A and the second needle assembly 280B. In other embodiments, the separation plate 276 can, for example, extend substantially the entire length of the elongate shaft 256. As shown in FIG. 18, the separation plate 276 is configured to traverse the elongate shaft 256 and coupled thereto. For example, the separation plate 276 includes a set of tabs 276A configured to be inserted and/or disposed in openings 263 defined by the elongate shaft 256 (e.g., defined by sidewalls of the elongate shaft 256). As such, the separation plate 276 can traverse the inner volume 258 of the elongate shaft 256, for example, to separate and/or isolate at least a portion of the inner volume 258. For example, although not shown in FIG. 18, the cartridge 250 includes at least one suture at least temporarily disposed within the inner volume 258 of the elongate shaft 256. Thus, by separating a portion of the inner volume 258, the elongate shaft 256 can house and/or store the suture in a substantially fixed position as the cartridge 250 is placed in a desired position within the body. Moreover, the suture can be separated from the other components disposed within the inner volume 258 such that motion of those components (e.g., the push rods 265A and 265B, etc.) do not engage the suture, which may otherwise result in damage to the suture.

As shown in FIG. 18, the central plate 278 is disposed about the pin 276 and between the first needle assembly 280A and the second needle assembly 280B. In this manner, the central plate 278 can provide structural rigidity to the distal end portion 252 of the cartridge 250. In addition, the central plate isolates the first needle assembly 280A from the second needle assembly 280B. As such, the first needle assembly 280A and the second needle assembly 280B can rotate about the axis A defined by the pin 276 substantially without interference (e.g., snagging, binding, friction, etc.) from the second needle assembly 280B and the first needle assembly 280A, respectively. Moreover, the central plate 278 and the one or more biased washers 279 can direct and/or bias the first needle assembly 280A and/or the second needle assembly 280B as the first needle assembly 280A and/or the second needle assembly 280B, respectively, rotate about the axis A defined by the pin 275.

Figure 20:
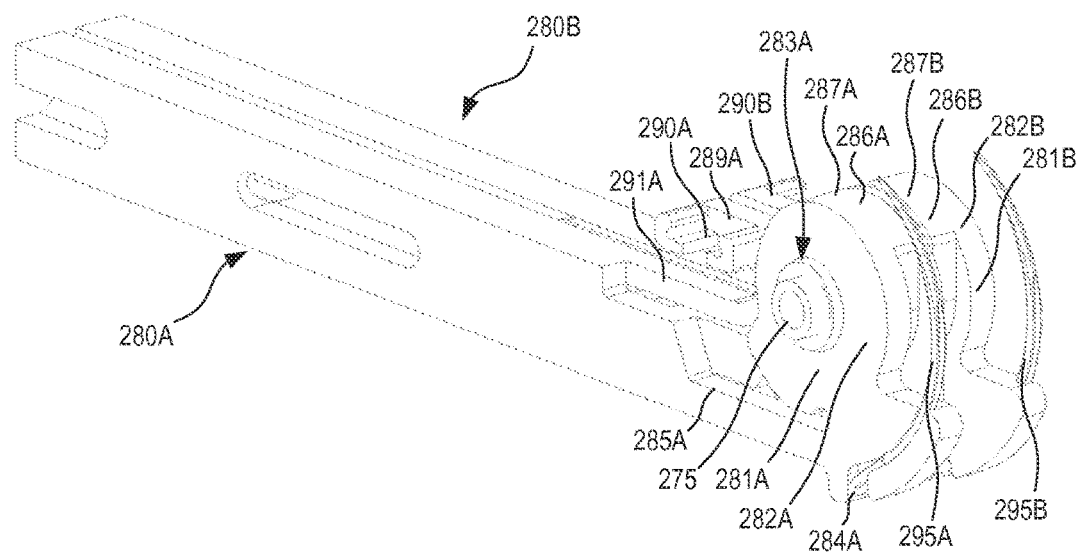
FIG. 20 is a perspective view of a first needle assembly and a second needle assembly included in the cartridge illustrated in FIG. 13.

The first needle assembly 280A and the second needle assembly 280B can be any suitable shape, size, or configuration. For example, as shown in FIGS. 20-28, the first needle assembly 280A includes a first portion 281A coupled to a needle 295A and a second portion 286A having a capture member 289A. The second needle assembly 280B similarly includes a first portion 281B coupled to a needle 295B and a second portion 286B handing a capture member 289B. The first needle assembly 280A and the second needle assembly 280B are substantially similar and are arranged, for example, in mirror orientations, as shown in FIG. 20. Thus, a discussion of the first needle assembly 280A with reference to FIGS. 20-28 is intended to apply to the second needle assembly 280B. Therefore, the second needle assembly 280B is not described in further detail herein and should be considered to be substantially similar in form and function to the first needle assembly 280A unless explicitly stated otherwise.

Figure 21:
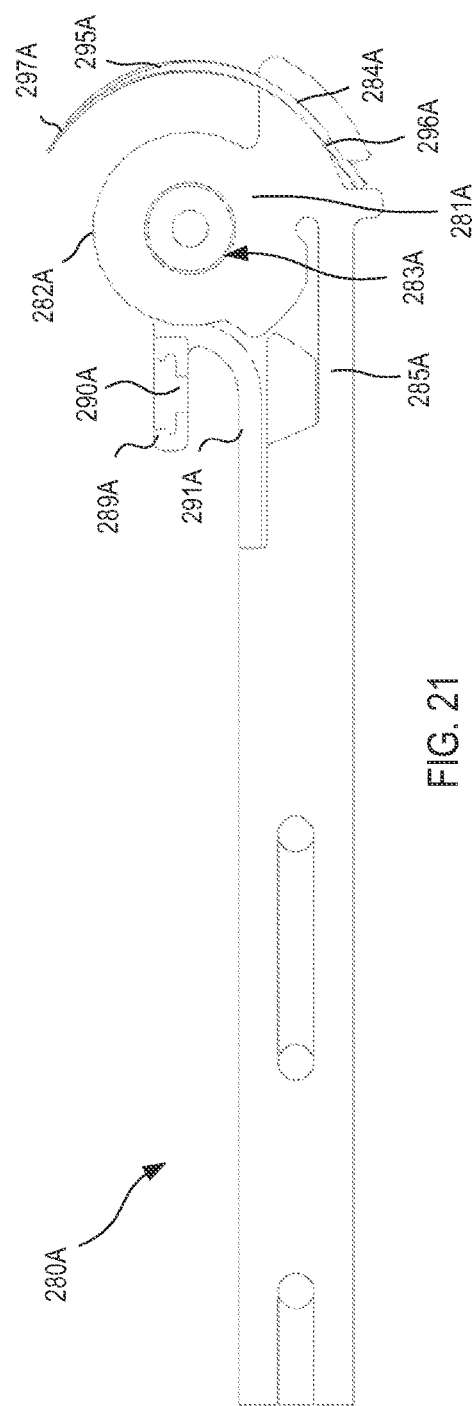
FIGS. 21 and 22 are a left side view and a right side view, respectively, of the first needle assembly illustrated in FIG. 20, in a first configuration.
Figure 22:
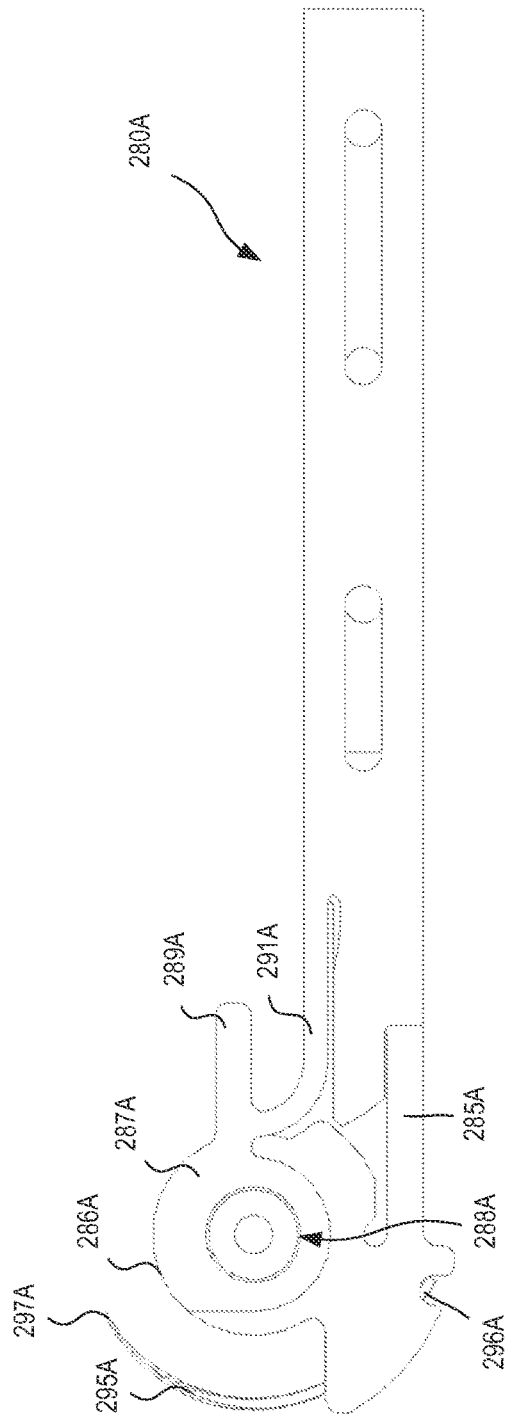

As described above, the first needle assembly 280A is disposed about the pin 275 at the distal end portion 252 of the cartridge 250 and is coupled to a distal end portion 267A of the first push rod 265. The first needle assembly 280A includes a first portion 281A and a second portion 286A, as shown in FIGS. 20-22. The first portion 281A and the second portion 286A can be arranged in any suitable manner. For example, in some embodiments, the first needle assembly 280A is partially bifurcated (e.g., about a plane associated with a midpoint along a width of the first needle assembly 280A, as shown in FIG. 20) into the first portion 281A and the second portion 286A. In this manner, the first portion 281A can be moved relative to the second portion 286A and/or vice versa, as described in further detail herein. Although described as being bifurcated, in other embodiments, the first needle assembly 280A can include the first portion 281A and the second portion 282A arranged in a non-bifurcated arrangement.

The first portion 281A includes a cam 282A defining an opening 283A and a slot 284A. The cam 282A is disposed about the pin 275A. In other words, the opening 283A receives a portion of the pin 275A to rotatably couple the cam 282A to thereto. The slot 284A receives a first end portion 296A of a needle 295A, as shown in FIG. 21. As described in further detail herein, the first end portion 296A of the needle 295A is temporarily disposed within the slot 284A and is configured to be removed from the slot 284A when the first needle assembly 280A is transitioned to the second configuration. The first portion 281A of the first needle assembly 280A further includes a deformable member 285A. As described above with reference to the deformable portion 233A of the first arm 231A of the actuator 230A, the deformable member 285A of the first portion 281A of the first needle assembly 280A is configured to deform in response to an applied force. More specifically, when a force is exerted on the engagement portion 232A of the first arm 231A, the coupling portion 234A moves in the distal direction, which in turn, moves the first push rod 265A in the distal direction. Therefore, with the first needle assembly 280A coupled to the distal end portion 267A of the first push rod 265A, the distal movement of the first push rod 265A exerts force on the first needle assembly 280A that is sufficient to bend, flex, deflect, and/or otherwise deform the deformable member 285A. As such, the deformable member 285A of the first portion 281A can form and/or otherwise act as a living hinge configured to deform in response to the applied force to rotate the first portion 281A of the first needle assembly 280A about the axis A defined by the pin 275 in a first direction, as described in further detail herein.

As shown in FIG. 22, the second portion 286A of the first needle assembly 280A includes a cam 287A defining an opening 288A. As described above with reference to the first portion 281A, the opening 288A receives a portion of the pin 275A to rotatably couple the cam 287A of the second portion 286A thereto. The arrangement of the first portion 281A and the second portion 286A about the pin 275A is such that at least the cam 282A of the first portion 281A is coaxial with the cam 287A of the second portion 286A. Thus, in response to an applied force, the cams 282A and 287A are configured to rotate about the axis A defined by the pin 275A, as described in further detail herein. The second portion 286A further includes a capture member 289A and a deformable member 291A. As described above with reference to the deformable member 285A of the first portion 281A, the deformable member 291A of the second portion 286A is configured to bend, flex, deflect, and/or otherwise deform in response to an applied force. Thus, the deformable portion 291A of the second portion 286A can form and/or otherwise act as a living hinge configured to deform in response to the applied force to rotate the second portion 286A of the first needle assembly 280A about the axis A defined by the pin 275 in a second direction (e.g., opposite the first direction), as described in further detail herein.

The capture member 289A of the second portion 286A can be any suitable shape, size, and/or configuration. For example, as shown in FIGS. 21 and 22, the capture member 289A can be a tab or protrusion that defines an opening 290A. As described in further detail herein, the capture member 289A is configured to receive a second end portion 297A of the needle 295A to engage and/or capture the needle 295A as the first needle assembly 280A is transitioned from its first configuration to its second configuration. Although not shown, the capture member 289A can have any suitable shape or configuration and/or can include any suitable member or feature configured to capture the needle 295A to maintain the needle 295A in a substantially fixed position relative to the capture member 289A. For example, in some embodiments, the capture member 289A can include an insert or the like (e.g., a metal insert coupled to the capture member 289A) configured to wedge or trap the needle 295A into a desired position relative to the capture member 289A. That is to say, the insert and the needle 295A can collectively form a friction fit or the like operative to retain the needle 295A in a substantially fixed position relative to the capture member 289A. In other embodiments, the needle 295A can be inserted into the opening 290A of the capture member 289A in such a manner that a portion of the capture member 289A defining the opening 290A forms a friction fit with the needle 295A. In still other embodiments, the capture member 289A can include a membrane, a set of protrusions, tabs, or fingers, and/or any other suitable feature configured to engage a portion of the needle 295A to at least temporarily retain the needle 295A in a fixed position relative to the capture member 289A.

As described above, the second needle assembly 280B is substantially similar to the first needle assembly 280A and is configured to be moved and/or reconfigured in substantially the same manner (as described in further detail herein). Thus, the second needle assembly 280B includes a first portion 281B having a cam 282B and a deformable member 285B, and a second portion 286B having a cam 287B, a capture member 289B, and a deformable member 291B. The first portion 281B defines an opening 283B configured to receive a portion of the pin 275 and a slot 284B configured to receive a first end portion 296B of a needle 295B. The second portion 286B defines an opening 288B configured to receive a portion of the pin 275. The capture member 289B defines an opening 290B. The capture member 289B is configured to receive a second end portion 297B of the needle 295B to engage and/or capture the needle 295B when the second needle assembly 280B is transitioned from the first configuration to the second configuration. Moreover, the second needle assembly 280B is coupled to a distal end portion 267B of the second push rod 265B. In this manner, the second needle assembly 280B can be substantially similar in form and function as the first needle assembly 280A described in detail above.

Figure 27:
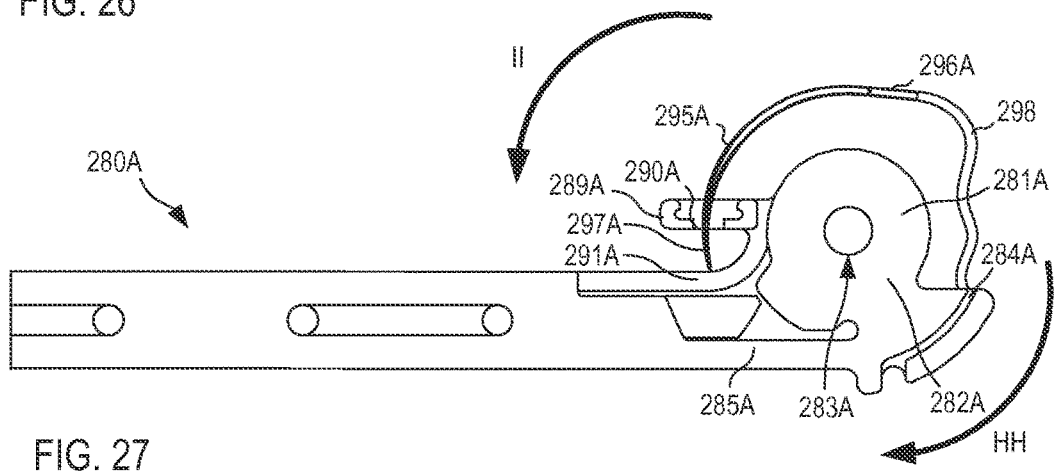
FIG. 27 is a side view of the first needle assembly of FIG. 20 in a third configuration.
Figure 28:
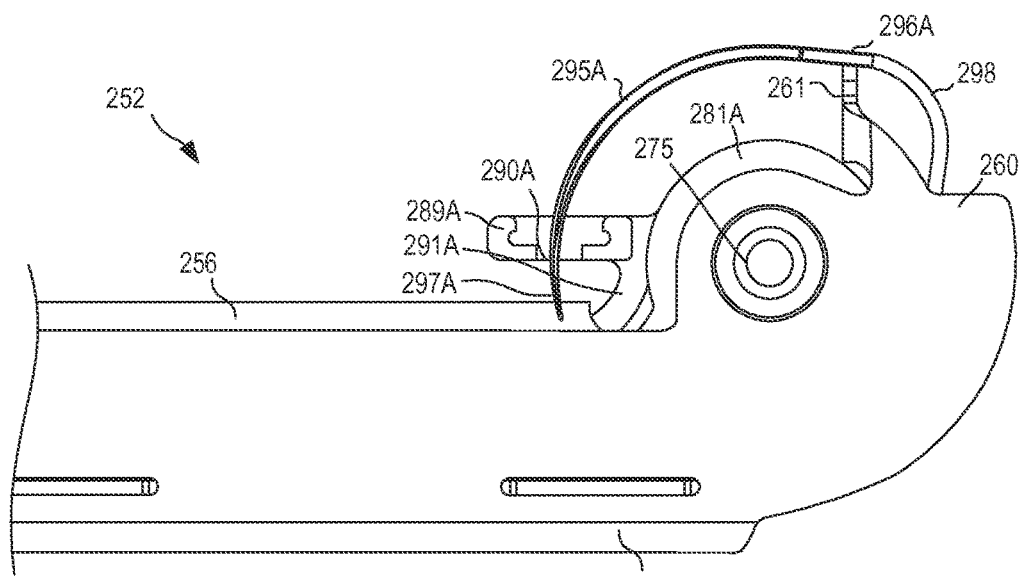
FIG. 28 is a side view of the distal end portion of the dural repair device of FIG. 3 in the third configuration.

The needle 295A of the first needle assembly 280A and the needle 295B of the second needle assembly 280B are coupled to a first end and a second end, respectively, of a suture 298 (partially shown, for example, in FIGS. 27 and 28). In other words, the distal end portion 252 of the cartridge 250 includes a single suture 298 having a first end coupled to the first end portion 296A of the needle 295A and a second end coupled to the first end portion 296B of the needle 295B. As described above, in some embodiments, the suture 298 can be at least temporarily stored and/or housed within a portion of the inner volume 258 of the elongate shaft 256 (e.g., the portion of the inner volume 258 defined at least in part by the separation plate 276. As described in further detail herein, the device 200 can be placed in a desired position within the body and can be actuated to transition the first needle assembly 280A and/or the second needle assembly 280B from the first configuration to the second configuration and as such, advance the needles 295A and/or 295B, respectively, and at least the ends of the suture 298 through a target tissue. Thus, the device 200 can be used to place one or more sutures in a target tissue.

More specifically, in use, a user such as a surgeon or the like can manipulate the device 200 by coupling the proximal end portion 251 of the cartridge 250 to the distal end portion 207 of the handle 205 (see e.g., FIG. 15). As described in detail above, coupling the cartridge 250 to the handle 205 operably couples the actuator 230 to the cartridge 250. With the cartridge 250 coupled to the handle 205, the user can manipulate the device 200 by inserting the cartridge into, for example, an incision in a patient and placing the distal end portion 252 of the cartridge 250 in a desired position relative to a target tissue. For example, in some embodiments, the device 200 can be used in a repair procedure in which a portion of a target tissue such as, for example, dura mater, on a first side of a tear therein is sutured to a portion of the target tissue on a second side of the tear. In such embodiments, the distal end portion 252 of the cartridge 250 can be placed on a distal side (e.g., relative to the device 200 or the user and/or otherwise on an inner side) of the dura mater on the first side of the tear. Moreover, in some instances, the distal end portion 252 of the cartridge 250 can be positioned such that a proximal surface of the distal tip 261 (see e.g., FIG. 19) is in contact with the distal surface of the portion of the target tissue. In some embodiments, the distal tip 261 can be configured to at least partially stabilize the dura mater as the device 200 is in use.

Once in a desired position, the user can place and/or otherwise ensure that the lock 240 is in a configuration associated with preventing movement of the second arm 231B of the actuator 230. In other words, the user can place the selector 241 in a position associated with preventing movement of the second arm 231B of the actuator 230 (as described above with reference to FIGS. 11 and 12). With the lock 240 in the desired configuration, the user can exert a force on, for example, the engagement portion 232A of the first arm 231A to cause the first arm 231A to pivot relative to the handle 205, as indicated by the arrow BB in FIG. 23. As described above, at least a portion of the force exerted by the user deforms the deformable portion 233 (e.g., the living hinge) of the first arm 231A, which in turn, is operative to transform the pivoting motion of the engagement portion 232A into a translational motion of the coupling portion 234A in the distal direction. The distal movement of the coupling portion 234A moves the first push rod 265 in the distal direction, as indicated by the arrow CC in FIG. 23, which in turn, exerts at least a portion of the force exerted by the user on the first needle assembly 280A.

Figure 23:
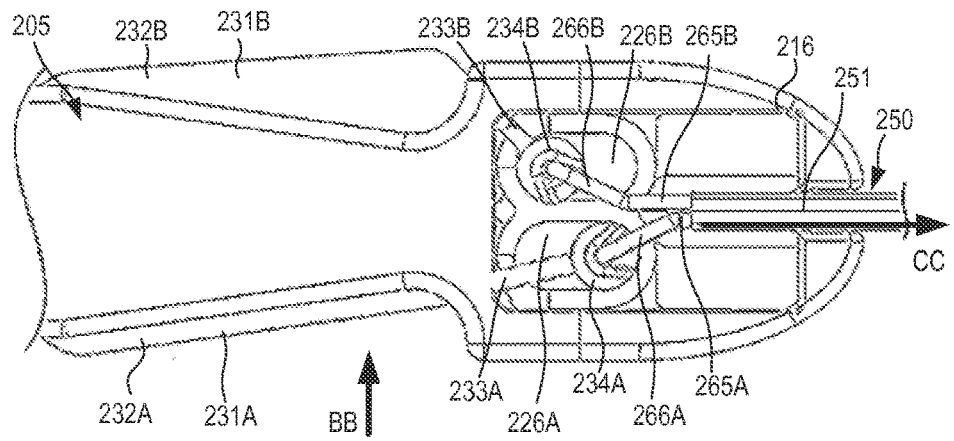
FIG. 23 is a top view of a portion of the dural repair device of FIG. 3 in a second configuration.

The force exerted on the first needle assembly 280A is sufficient to deform the deformable members 285A and 291A of the first portion 281A and the second portion 286A, respectively, to transition the first needle assembly 280A from the first configuration to the second configuration. Specifically, the deformation (e.g., bending, flexing, deflecting, and/or reconfiguring) of the deformable member 285A of the first portion 281A exerts a portion of the force on the cam 282A of the first portion 281A, which results in the cam 282A rotating about the axis A defined by the pin 275 in the first direction, as indicated by the arrow DD in FIG. 24. Similarly, the deformation (e.g., bending, flexing, deflecting, and/or reconfiguring) of the deformable member 291A of the second portion 286A exerts a portion of the force on the cam 287A of the second portion 286A, which results in the cam 287A rotating about the axis A defined by the pin 275 in the second direction, as indicated by the arrow EE in FIG. 24. Thus, the force exerted by the user on the first arm 231A is operative to rotate the capture member 289A and the needle 295A of the first needle assembly 280A about the axis A defined by the pin 275, which in turn, transitions the first needle assembly 280A from the first configuration to the second configuration. With the distal end portion 252 of the cartridge 250 in the desired position within the body, the rotation of the needle 295A advances at least a portion of the needle 295A through the target tissue (not shown) such that at least a portion of the needle 295A is disposed on a proximal side of the target tissue (e.g., opposite the side of the target tissue when the first needle assembly 280A was in the first configuration), which in turn, places the device 200 in its second configuration (see e.g., FIG. 23, illustrating the distal end portion 207 of the handle 205 and FIG. 25 illustrating the distal end portion 252 of the cartridge 250 when the device 200 is in the second configuration).

In some instances, the capture member 289A can be placed in contact with a surface of the target tissue (e.g., an outer surface) as the first needle assembly 280A is placed in the second configuration. As described above, the distal end portion 252 of the cartridge 250 can be positioned relative to the target tissue such that the distal tip 261 is also in contact with a surface of the target tissue (e.g., an inner surface and/or a surface opposite the surface in contact with the capture member 289A). Thus, the target tissue can be disposed between and in contact with the distal tip 261 and the capture member 289A as the device 200 is transitioned to the second configuration. In some instances, this arrangement can, for example, at least partially stabilize the target tissue to facilitate the advancing of the needle 295A therethrough.

Figure 24:
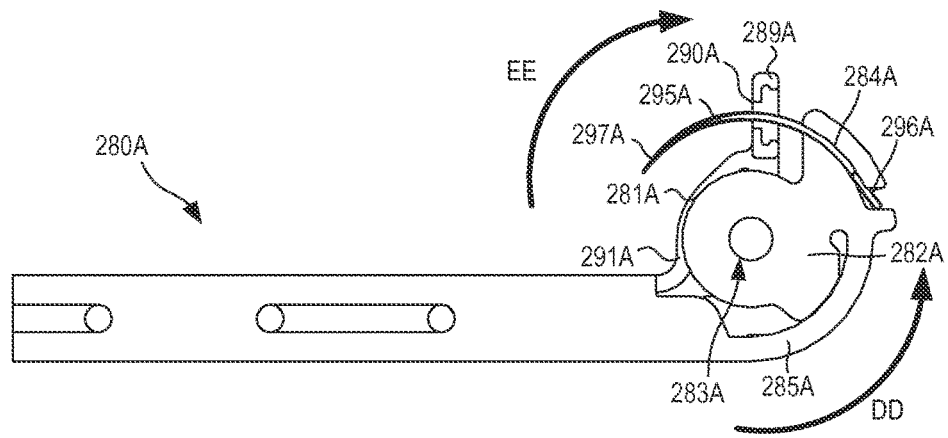
FIG. 24 is a left side view of the first needle assembly illustrated in FIG. 20, in a second configuration.
Figure 25:
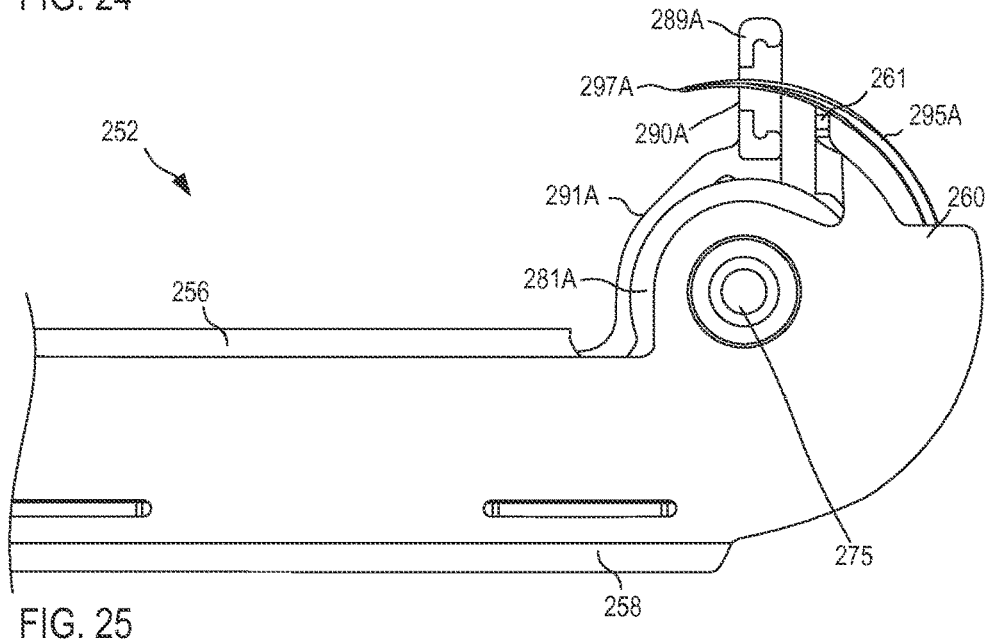
FIG. 25 is a side view of the distal end portion of the dural repair device of FIG. 3 in the second configuration.

As described above, the capture member 289A and the needle 295A are placed in contact when the first needle assembly 280A is placed in its second configuration, as shown in FIGS. 24 and 25. More specifically, the capture member 289A can capture, retain, secure, and/or otherwise couple to the needle 295A when the first needle assembly 280A is in the second configuration. In other words, the capture member 289A can be placed in contact with a portion of the needle 295A when the first needle assembly 280A is placed in the second configuration such that the needle 295A is retained in a substantially fixed position relative to the capture member 289A. Although not shown in FIGS. 24 and 25, the capture member 289A can have and/or can include a geometry, plate, trap, wedge, contour, membrane, etc. configured to secure and/or capture the needle 295A and retain the needle 295 in a substantially fixed position relative to the capture member 289A when needle 295A is placed in contact therewith.

Figure 26:
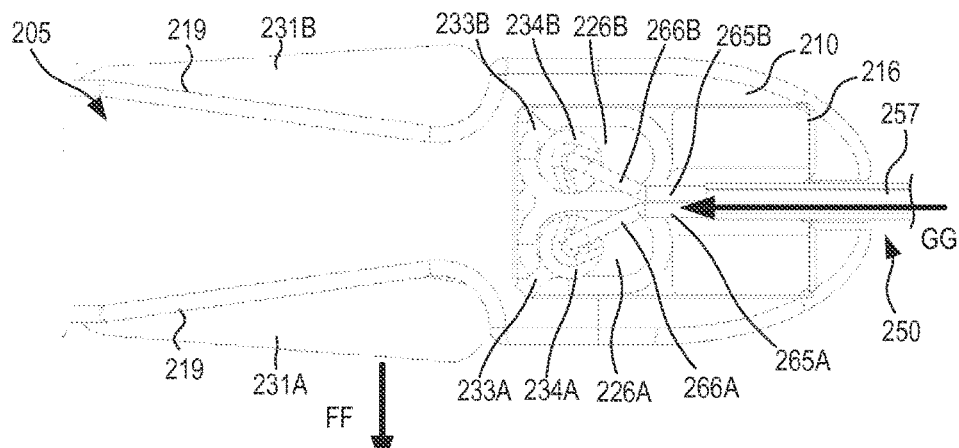
FIG. 26 is a top view of a portion of the dural repair device of FIG. 3 in a third configuration.

With the first needle assembly 280A in its second configuration, the user can remove the force exerted on the first arm 231A, and thus, the engagement portion 232A can pivot relative to the handle 205, as indicated by the arrow FF in FIG. 26. For example, although not shown herein, the first arm 231A can be coupled to a bias member or the like that biases the first arm 231A toward its first configuration. Therefore, when the user removes the force exerted on the first arm 231A, the first arm 231A transitions from its second configuration to its first configuration. The movement of the first arm 231A in response to the removal of the force results in the first push rod 265 moving in the proximal direction, as indicated by the arrow GG in FIG. 26, which in turn, removes the force otherwise exerted on the first needle assembly 280A.

With the force removed from the first needle assembly, the deformable portion 285A and 291A transition from their deformed state back to a substantially undeformed state. That is to say, while the deformable portions 285A and 291A are configured to elastically deform, the deformable portions are nonetheless biased toward an undeformed state. Thus, the first portion 281A of the first needle assembly 280A rotates about the axis A defined by the pin 275 in a direction substantially opposite the first direction (as indicated by the arrow HH in FIG. 27) and the second portion 286A of the first needle assembly 280A rotates about the axis A in a direction substantially opposite the second direction (as indicated by the arrow II in FIG. 27). With the needle 295A captured and/or retained by the capture member 289A, however, the needle 295A rotates concurrently and in the same direction with the capture member 289A, which in turn, transitions the device 200 from its second configuration to its third configuration. As shown in FIGS. 27 and 28, the rotation of the needle 295A with the capture member 289A is such that the first end portion 296A of the needle 295A is removed from and/or pulled out of slot 284A defined by the first portion 281A of the first needle assembly 280A such that the needle 295A is further advanced through the target tissue. In some instances, the rotation of the needle 295A can be sufficient to advance the first end portion 296A at least a portion of the suture 298 through the target tissue. In other instances, the needle 295A is substantially advanced through the target tissue and, for example, the user can move the device 200 (e.g., slightly) to pull the first end portion 296A of the needle 295A and at least a portion of the suture 298 through the target tissue.

With a portion of the suture extending through the target tissue, the user can manipulate the device 200 to place the distal end portion 252 of the cartridge 250 on a distal side of the portion of the target tissue on the second side of the tear. Once in a desired position, the user can place and/or otherwise ensure that the lock 240 is in a configuration associated with preventing movement of the first arm 231A of the actuator 230 while not inhibiting movement of the second arm 231B of the actuator 230, as described above with reference to FIGS. 11 and 12. With the lock 240 in the desired configuration, the user can exert a force on the engagement portion 232B of the second arm 231B. As described above with reference to the first arm 231A and the first needle assembly 280A, the force exerted on the second arm 231B is sufficient to place the second needle assembly 280B in its second configuration. Thus, the needle 295B of the second needle assembly 280B is advanced through the target tissue such that at least a portion of the needle 295B is disposed on a proximal side of the target tissue, as described above with reference to the first needle assembly 280A. The user can then remove the force exerted on engagement portion 232B of the second arm 231B to transition the second needle assembly 280B from its second configuration to its third configuration, as described in detail above with reference to the first needle assembly 280A.

With the first needle assembly 280A and the second needle assembly 280B in their second configurations, the user can withdraw the device 200 from the body. Thus, the suture 298 can be pulled to close at least a portion of the tear in the target tissue and once that portion is substantially closed, the user can tie a knot in the suture 298, thereby suturing the tear in the target tissue. In other embodiments, the user can close the tear and place a knot in the suture 298 prior to removing the device 200 from the body. In some embodiments, the device 200 can be configured to form the knot at least semi-automatically after the needles 295A and 295B have been advanced through the target tissue. In some instance, the user can place the knot in the suture 298 in a proximal position relative to the target tissue. In such instances, the user can use, for example, a knot pusher or the like to push the knot in the distal direction toward the target tissue, thereby cinching the knot down onto the target tissue.

By way of example, FIGS. 29 and 30 illustrate a knot pusher 201 that can be used to push the knot formed in the suture 298. As shown, the knot pusher 201 includes a proximal end portion 202 and a distal end portion 203. The proximal end portion 202 can be any suitable shape, size, and/or configuration. For example, in this embodiments, the proximal end portion 202 of the knot pusher 201 forms a ring or the like. In some embodiments, the arrangement of the proximal end portion 202 can have an ergonomic design configured to facilitate use of the knot pusher 201. The distal end portion 203 of the knot pusher 201 can be any suitable shape, size, and/or configuration. For example, in this embodiment, the distal end portion 203 can have a bend configured to provide a desired alignment during use. As shown in FIG. 30, the distal end portion 203 defines an opening 204. The opening 204 is configured to receive the ends of the suture 298 and thus, the knot pusher 201 can be disposed in an immediate proximal position relative to the knot formed in the suture 298 and can be moved along a length of the suture 298 to cinch the knot down onto the target tissue. In the embodiment shown in FIG. 30, the opening 204 extends through a side of the distal end portion 203 of the knot pusher 201. In other embodiments, the opening 204 can be, for example, an aperture or bore (e.g., that does not extend through a side of the knot pusher 201). Thus, the device 200 and the knot pusher 201 can be used collectively to place one or more sutures in a target tissue.

Figure 31:
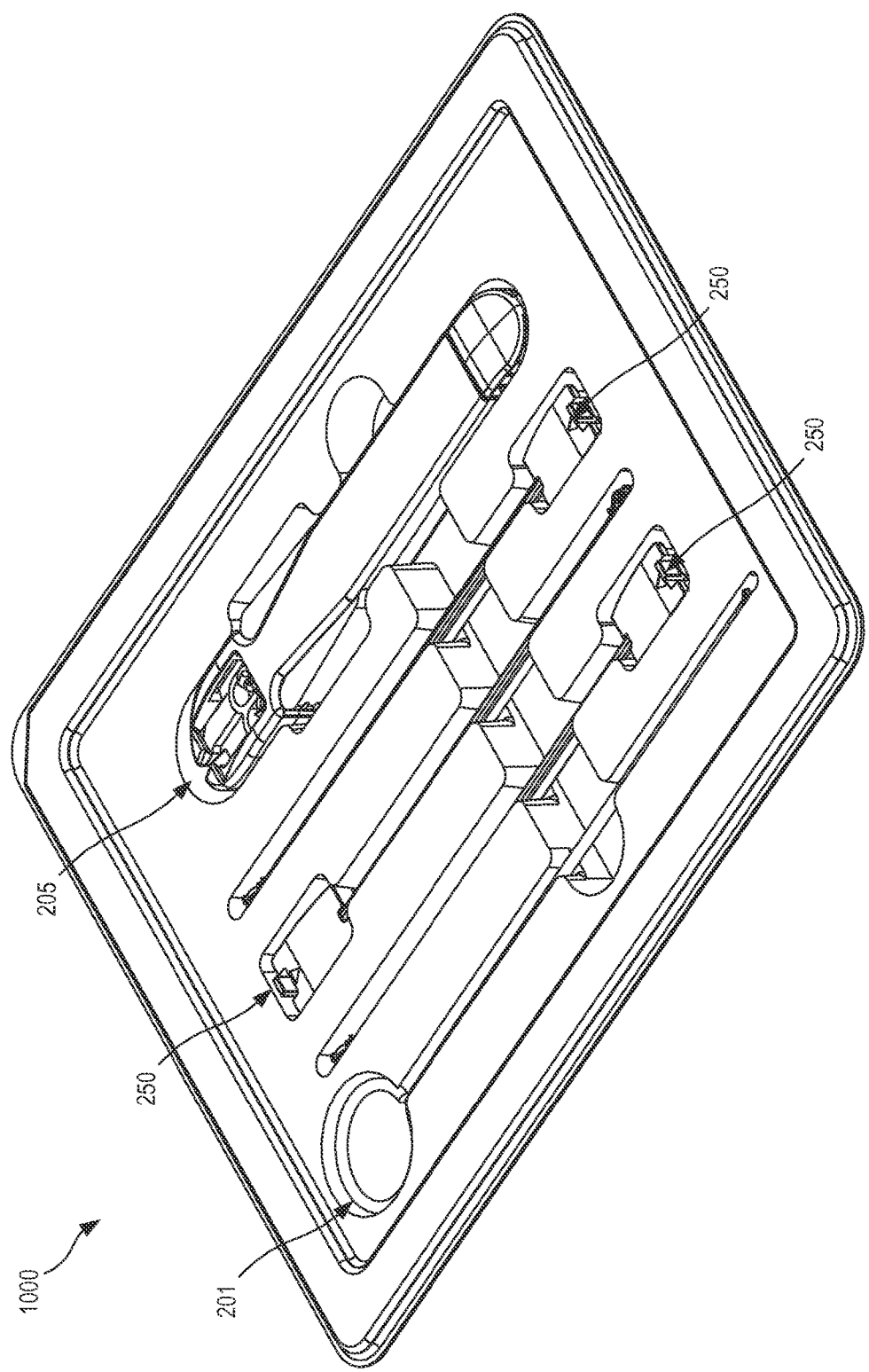
FIG. 31 is a perspective view of a kit including the dural repair device of FIG. 3 and the knot pusher of FIG. 29.
Figure 32:
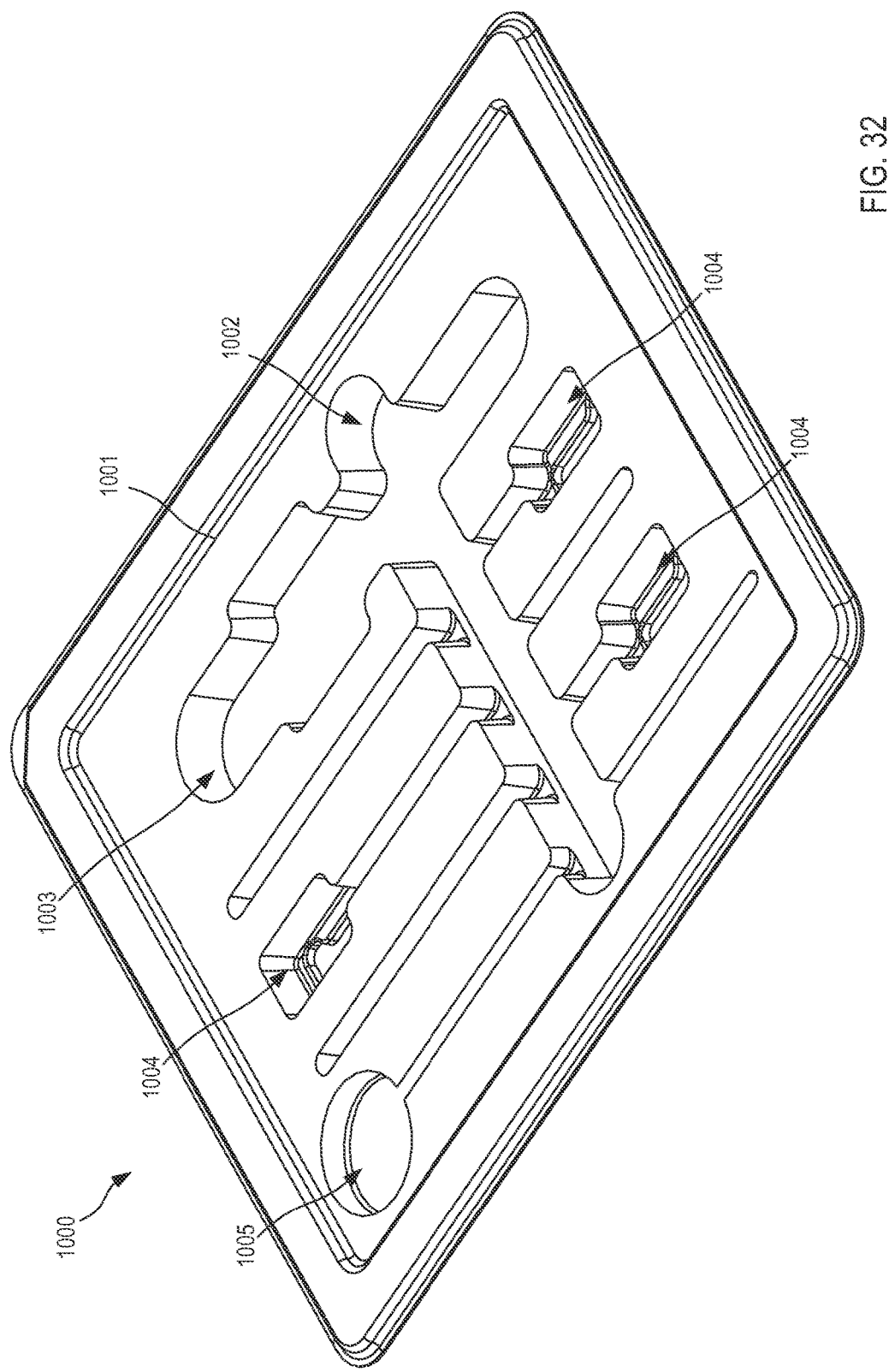
FIG. 32 is a perspective view of a packaging included in the kit of FIG. 31.

In some instances, the device 200 (i.e., the handle 205 and one or more cartridges 250) can be included in a substantially sterile packaging or the like prior to use. For example, FIGS. 31 and 32 illustrate a substantially sterile packaging 1000 configured to maintain, for example, the handle 205, a set of cartridges 250, and the knot pusher 201 in a substantially sterile environment prior to use. More specifically, the substantially sterile packaging 1000 (also referred to herein as "packaging") includes a tray 1001 defining a contour 1002. In this embodiment, the contour 1002 of the tray 1001 defines a handle portion 1003, a set of cartridge portions 1004, and a knot pusher portion 1005. In some embodiments, during a manufacturing process, the handle 205 can be positioned within the handle portion 1003, at least one cartridge 250 can be positioned within the set of cartridge portions 1004, and the knot pusher 201 can be positioned within the knot pusher portion 1005, as shown in FIG. 31. For example, such a manufacturing process can be performed in an ethylene oxide environment or the like configured to sterilize the packaging 1000, the handle 205, the at least one cartridge 250, and the knot pusher 201. Although not shown in FIGS. 31 and 32, the packaging 1000 includes a seal and/or cover that is coupled to the tray 1001, for example, while the packaging 1000 is disposed in the substantially sterile environment and after the handle 205, the at least one cartridge 250, and the knot pusher 201 are disposed in the tray 1001. In this manner, the packaging 1000 can maintain the device 200 and the knot pusher 201 in a substantially sterile environment until a user removes and/or decouples the seal and/or cover from the tray 1001. Said another way, the device 200 (e.g., the handle 205 and at least one cartridge 250) and the knot pusher 201 can be packaged and sold together as a kit configured to maintain the sterility of the device 200 and the knot pusher 201 until the user removes the seal and/or cover from the tray 1001.

While the packaging 1000 is shown in FIGS. 31 and 32 as receiving three cartridges 250, in other embodiments, the contour 1002 of the tray 1001 can define more than three cartridge portions 1004 or less than three cartridge portions 1004. While the packaging 1000 is shown as receiving the device 200, any number of extra cartridges 250, and the knot push 201, in other embodiments, a packaging can include only the handle 205, only the device 200 (e.g., the handle 205 and one cartridge 250), only the device 200 and extra cartridges 250, only a set of cartridges 250, or only the knot pusher 1005. Said another way, the handle 205, the cartridge 250, and the knot pusher 201 can be packaged together or separately and/or in any suitable combination thereof. By way of example, in embodiments in which the handle 205 is non-fungible (e.g., reusable), the handle 205 can be packaged and sold independent from the cartridges 250 and the knot pusher 201. In such embodiments, a set of cartridges 250 and the knot pusher 201 can be, for example, packaged and sold as a kit for use with the reusable handle 205.

In some instances, a tear in a target tissue can call for more than one suture. In such instances, the user can, after placing the first suture, decouple the cartridge 250 from the handle 205 and can couple an unused cartridge 250 to the handle 205. Thus, the user can perform substantially the same procedure as described above to place any suitable number of sutures within a target tissue. In other embodiments, the handle 205 and the cartridge 250 can be discarded after placing the first suture and a new handle 205 and cartridge 250 can be used in substantially the same procedure to place any number of subsequent sutures. In still other embodiments, the cartridge 250 can be configured to place any number of sutures. For example, in some embodiments, after the user places a first suture using the device 200, the device 200 can be reset and/or otherwise transitioned into the first configuration such that the needles 295A and 295B are coupled to a new suture and at least partially disposed within the slot 284A defined by the first needle assembly 295A and the slot 284B defined by the second needle assembly 295B, respectively. In still other embodiments, the device 200 can be used to place a running suture, in which one suture is passed through a target tissue multiple times in, for example, a tacking or zigzag motion.

Figure 33:
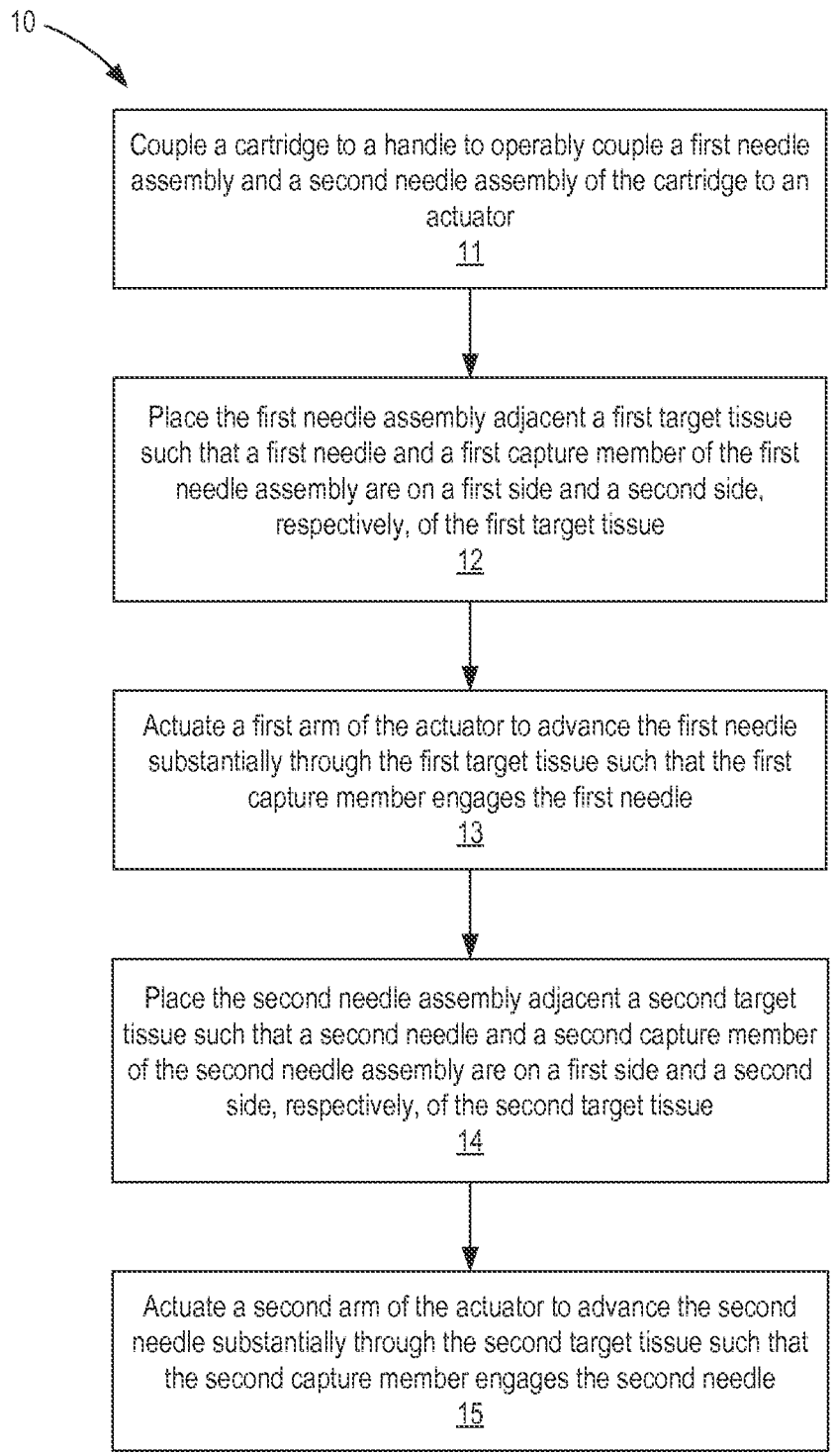
FIG. 33 is a flowchart illustrating a method of using a dural repair device according to an embodiment.

Referring now to FIG. 33, a flowchart illustrates a method 10 of using a repair device to, for example, place one or more sutures within a target tissue. The repair device can be any suitable device such as, for example, those described herein. In some embodiments, the repair device can include a handle (e.g., the handle 205) including a lock and an actuator and a cartridge (e.g., the cartridge 250) including a first needle assembly, a second needle assembly, and at least one suture. The repair device can be used in any suitable procedure such as, for example, a procedure to suture a tear or cut in the dural mater. The method 10 includes coupling the cartridge to the handle to operably couple the first needle assembly and the second needle assembly of the cartridge to the actuator included in the handle, at 11.

With the cartridge coupled to the housing, the first needle assembly is placed adjacent a first target tissue such that a first needle and a first capture member of the first needle assembly are on a first side and a second side, respectively, of the first target tissue, at 12. For example, the first needle assembly and the second needle assembly can be disposed at or near a distal end portion of the cartridge. Thus, the user can manipulate the device to place at least the distal end portion of the cartridge in a desired position within the body of a patient. In some instances, the first target tissue can be dura mater disposed on and/or defining a first portion of a tear. In such instances, the first side and the second side of the first target tissue can be, for example, a distal or inner surface of the dura mater and a proximal or outer surface of the dura mater, respectively.

After positioning the first needle assembly in the desired position, a first arm of the actuator is actuated to advance the first needle substantially through the first target tissue such that the first capture member engages the first needle, at 13. For example, in some embodiments, the repair device is substantially similar to the device 200. In such embodiments, the first needle assembly (or portions thereof) can be transitioned from a first configuration in which the first needle and the first capture member are separated to a second configuration in which the first capture member engages and/or captures the first needle. More specifically, the actuation of the first arm results in a force being exerted on the first needle assembly sufficient to deform one or more portions of the first needle assembly such that a first portion of the first needle assembly associated with the first needle and a second portion of the first needle assembly associated with the first capture member are rotated about an axis in substantially opposite directions. Thus, rotating the first portion and the second portion of the first needle assembly transitions the first needle assembly from the first configuration to the second configuration.

In some embodiments, the first capture member engages the first needle to maintain the first needle in a substantially fixed position relative thereto. As described above, once the first needle is at least partially advanced through the first target tissue, the user can remove the force from the first arm of the actuator. As such, the first needle assembly can be transitioned from the second configuration to a third configuration. As described above with reference to the device 200, in some embodiments, the third configuration can be similar to the first configuration; however, the capture member maintains engagement with the first needle when the first needle assembly is transitioned from the second configuration to the third configuration. In such embodiments, the first needle can be decoupled from, for example, the first portion of the first needle assembly. Moreover, when the first needle assembly is in the third configuration, the first needle can be advanced through the first target tissue to be disposed on the second side, which in turn, advances a first end portion of the suture through the first target tissue such that the first end portion the suture is disposed on the second side of the first target tissue.

With the suture advanced through the first target tissue, the second needle assembly is placed adjacent to the second target tissue such that a second needle and a second capture member of the second needle assembly are on a first side and a second side, respectively, of the second target tissue, at 14. For example, the second target tissue can be dura mater disposed on and/or defining a second portion of the tear (described above). In such instances, the first side and the second side of the second target tissue can be, for example, a distal or inner surface of the dura mater and a proximal or outer surface of the dura mater, respectively. Although not shown in FIG. 33, in some embodiments, the method can optionally include transitioning the lock included in the handle from a from a first lock configuration in which the lock substantially limits movement of a second arm of the actuator to a second lock configuration in which the lock substantially limits movement of the first arm of the actuator.

Once the second needle assembly is placed in a desired position relative to the second target tissue (and optionally once the lock is placed in the second lock configuration), the second arm of the actuator is actuated to advance the second needle substantially through the second target tissue such that the second capture member engages the second needle, at 15. As described above with reference to the first arm of the actuator and the first needle assembly, the actuation of the second arm of the actuator can transition the second needle assembly from this first configuration to the second configuration. Moreover, as described above, the force exerted on the second arm can be removed from the second arm of the actuator once the second needle is at least partially advanced through the second target tissue and thus, the second needle assembly can transition from the second configuration to its third configuration. As such, a second end portion of the suture can be advanced through the second target tissue such that the second end portion of the suture is disposed on the second side of the second target tissue.

Although not shown in FIG. 33, in some embodiments, the method 10 can also include tying a knot in the suture after the first end portion and the second end portion of the suture are advanced through the first target tissue and the second target tissue, respectively. For example, in some embodiments, the user can remove the device from the body of the patient and can tie a knot in the suture at a position proximal to the first target tissue and the second target tissue. With the knot tied in the suture, the user can, for example, use a knot pusher or the like configured to advance the knot along a length of the suture to cinch the knot on to the second side of the first target tissue and/or the second side of the second target tissue, which in turn can substantially close at least a portion of the tear or cut in the target tissue (e.g., the tear in the dura mater). In some embodiments, the method 10 can further include removing the cartridge from the handle and coupling a second cartridge (e.g., an unused cartridge) to the handle to place a second suture as just described. Moreover, the method 10 can be used to place any suitable number of sutures and/or any suitable kind of suture such as, for example, a running suture or the like.

The embodiments and methods described herein can be used to facilitate a medical professional (e.g., surgeon) in performing minimally invasive repairs of, for example, the dura mater. For example, the embodiments described herein can be designed for one-handed operation using the left hand or the right handed. By way of another example, the modular configuration of the embodiments described herein (e.g., the handle 205 and cartridge 250 of the device 200) can allow for relatively fast and simple assembly particularly when placing multiple sutures.

In addition, the embodiments described herein—more particularly, the cartridges—can have a size and/or configuration suitable for use in and/or with, for example, known tube retractor systems typically used in spinal surgeries and/or other minimally invasive surgeries without obstructing at least a portion of the repair site. While the embodiments and methods are specifically described above as being used in dural repair procedures, it is to be understood that the embodiments and methods described herein can be used in any other surgical operation such as, for example, minimally invasive surgeries typically involving working through small openings in bodily tissue. In some instances, the embodiments and methods described herein can be used to place one or more sutures in any suitable tubular anatomic structure such as, for example, a vein, artery, ureter, etc. Although described above as being used in minimally invasive surgical procedures, in some instances, the embodiments and methods described herein can be used in any suitable "open" surgery (i.e., surgeries not considered minimally invasive). The arrangement and/or configuration of the devices described herein can allow sufficient maneuverability of at least the distal end portion of the device to place the needle assemblies in desired positions relative to the tissue to be sutured.

While various embodiments have been described above, it should be understood that they have been presented by way of example only, and not limitation. Where schematics and/or embodiments described above indicate certain components arranged in and/or with certain sizes, orientations, or positions, the arrangement of components may be modified. For example, while the capture members 289A and 289B and the needles 295A and 295B have been described as being moved in a rotational motion about the axis A, in some embodiments, a device can include a set of capture members and/or needles configured to rotate about an axis as well as translate, for example, in a proximal and/or distal direction. For example, in some embodiments, such a device can include a set of capture members with each capture member configured to rotate to engage an associated needle and after capturing and/or engaging the needle, to translate in a proximal direction to, for example, pull the needle through a target tissue or the like. In still other embodiments, a device can include a set of capture members and needles configured to move only in a translational motion or in any suitable combination of rotational and translational motion.

By way of another example, while the distal end portion 258 of the elongate shaft 256 is shown in FIGS. 18 and 19 as covering and/or at least partially enclosing most of the first needle assembly 280 and the second needle assembly 280B, in other embodiments, the distal end portion 258 of the elongate shaft 256 can cover and/or at least partially enclose more or less of the first needle assembly 280 and/or the second needle assembly 280B. For example, in some embodiments, the distal end portion 258 of the elongate shaft 256 can extend further in the distal direction to cover or enclose more of the distal end portion 252 of the cartridge 250. In such embodiments, the distal end portion 258 of the elongate shaft 256 can provide, for example, greater protection against damage to surrounding tissue or structures such as nerves. In other embodiments, the distal end portion 258 of the elongate shaft 256 does not extend as far in the distal direction as shown in FIGS. 18 and 19. In such embodiments, a greater portion of the first needle assembly 280A and the second needle assembly 280B can be exposed (e.g., not covered), which in some instances, can allow for greater accessibility when performing a suture procedure in very tight places within the body.

While the embodiments have been particularly shown and described, it will be understood that various changes in form and details may be made. Although various embodiments have been described as having particular features and/or combinations of components, other embodiments are possible having a combination of any features and/or components from any of embodiments as discussed above. By way of example, while the selector 241 is described above as being configured to produce an audible click and/or a haptic indication associated with placing the selector 241 in its first position or its second position, in some embodiments, any portion of the device 200 can include one or more features configured to produce an audible, visual, and/or haptic feedback associated with that portion of the device 200 being placed in a given configuration. For example, although not shown in FIGS. 3-28, in some embodiments, the first arm 231A and/or the second arm 231B can include any suitable feature or combination of features configured to produce an indication (e.g., an audible indication such as a click or the like) when the first arm 231A and/or the second arm 231B, respectively, are placed in the second configuration and/or otherwise fully actuated.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed is:

1. An apparatus, comprising:
a handle having a proximal end portion and a distal end portion;
a cartridge having a proximal end portion and a distal end portion, the proximal end portion configured to be removably coupled to the distal end portion of the handle, the distal end portion of the cartridge having a first needle assembly and a second needle assembly each configured to be transitioned between a first configuration and a second configuration, the first needle assembly including a first needle and a first capture member, the second needle assembly including a second needle and a second capture member;
an actuator movably coupled to the handle, the actuator having a first coupling portion operably coupled to the first needle assembly when the cartridge is coupled to the handle and a second coupling portion operably coupled to the second needle assembly when the cartridge is coupled to the handle, the first coupling portion configured to move relative to the handle in response to a first force to transition the first needle assembly from the first configuration in which the first capture member is spaced apart from the first needle to the second configuration in which the first capture member engages the first needle, the second coupling portion configured to move relative to the handle in response to a second force to transition the second needle assembly from the first configuration in which the second capture member is spaced apart from the second needle to the second configuration in which the second capture member engages the second needle; and
a lock operably coupled to the actuator, the lock configured to selectively limit movement of the first coupling portion and the second coupling portion,
wherein the actuator includes a selector coupled to the lock, the selector configured to transition between a first configuration in which the lock limits movement of the second coupling portion and a second configuration in which the lock limits movement of the first coupling portion.

2. The apparatus of claim 1, wherein the handle defines a longitudinal axis, the distal end portion of the cartridge defining a rotational axis substantially perpendicular to the longitudinal axis when the cartridge is coupled to the handle, the first needle and the first capture member configured to rotate about the rotational axis when the first needle assembly is transitioned between the first configuration and the second configuration, the second needle and the second capture member configured to rotate about the rotational axis when the second needle assembly is transitioned between the first configuration and the second configuration.

3. The apparatus of claim 1, wherein the cartridge includes a first push rod and a second push rod, the first push rod having a proximal end portion configured to be removably coupled to the first coupling portion of the actuator when the cartridge is coupled to the handle and a distal end portion coupled to the first needle assembly,
the second push rod having a proximal end portion configured to be removably coupled to the second coupling portion of the actuator when the cartridge is coupled to the handle and a distal end portion coupled to the second needle assembly.

4. The apparatus of claim 1, wherein the first coupling portion is configured to move relative to the handle in a predetermined direction, the second coupling portion is configured to move relative to the handle in the predetermined direction.

5. The apparatus of claim 1, wherein the lock is configured to rotate relative to a portion of the actuator to selectively limit movement of the first coupling portion or the second coupling portion.

6. The apparatus of claim 1, wherein the actuator includes a first arm and a second arm, the first coupling portion included in the first arm, the second coupling portion included in the second arm.

7. The apparatus of claim 6, wherein the first force is exerted on the first arm, a portion of the first arm is configured to deform in response to the first force, the first coupling portion being moved relative to the handle as the portion of the first arm deforms, the second force is exerted on the second arm, a portion of the second arm is configured to deform in response to the second force, the second coupling portion being moved relative to the handle as the portion of the second arm deforms.

8. The apparatus of claim 1, wherein the first needle is coupled to a first end of a suture and the second needle is coupled to a second end of the suture, the cartridge configured to place a single suture in a target tissue.

9. The apparatus of claim 1, wherein the first needle is coupled to a first end of a suture and the second needle is coupled to a second end of the suture, the cartridge configured to place a plurality of sutures in a target tissue.

10. An apparatus, comprising:
a handle having a proximal end portion and a distal end portion;
a cartridge having a proximal end portion and a distal end portion, the proximal end portion configured to be removably coupled to the distal end portion of the handle, the distal end portion of the cartridge having a first needle assembly and a second needle assembly each configured to be transitioned between a first configuration and a second configuration, the first needle assembly including a first needle and a first capture member, the second needle assembly including a second needle and a second capture member;
an actuator movably coupled to the handle, the actuator having a first coupling portion operably coupled to the first needle assembly when the cartridge is coupled to the handle and a second coupling portion operably coupled to the second needle assembly when the cartridge is coupled to the handle, the first coupling portion configured to move relative to the handle in response to a first force to transition the first needle assembly from the first configuration in which the first capture member is spaced apart from the first needle to the second configuration in which the first capture member engages the first needle, the second coupling portion configured to move relative to the handle in response to a second force to transition the second needle assembly from the first configuration in which the second capture member is spaced apart from the second needle to the second configuration in which the second capture member engages the second needle; and a lock operably coupled to the actuator, the lock configured to selectively limit movement of the first coupling portion and the second coupling portion, wherein the distal end portion of the cartridge defines a rotational axis, the first needle being in a first rotational needle position and the first capture member being in a first rotational capture member position when the first needle assembly is in the first configuration, the first needle and the first capture member being placed in a second rotational needle position and a second rotational capture member position, respectively, when the first needle assembly is in the second configuration, the first needle assembly configured to transition from the second configuration to a third configuration in response to a removal of the first force, the first capture member configured to rotate from the second rotational capture member position to the first rotational capture member position when the first needle assembly is transitioned from the second configuration to the third configuration, the first capture member configured to engage the first needle such that the first needle rotates with the first capture member from the second rotational needle position to a third rotational needle position when the first needle assembly is transitioned from the second configuration to the third configuration.

11. The apparatus of claim 10, wherein the second needle is in a first rotational needle position and the second capture member is in a first rotational capture member position when the second needle assembly is in the first configuration, the second needle and the second capture member being placed in a second rotational needle position and a second rotational capture member position, respectively, when the second needle assembly is in the second configuration, the second needle assembly configured to transition from the second configuration to a third configuration in response to a removal of the second force, the second capture member configured to rotate from the second rotational capture member position to the first rotational capture member position when the second needle assembly is transitioned from the second configuration to the third configuration, the second capture member configured to engage the second needle such that the second needle rotates with the second capture member from the second rotational needle position to a third rotational needle position when the second needle assembly is transitioned from the second configuration to the third configuration.

12. An apparatus, comprising:

a handle having a proximal end portion and a distal end portion, the handle defining a first channel and a second channel;

a cartridge having a proximal end portion and a distal end portion, the proximal end portion configured to be removably coupled to the distal end portion of the handle, the distal end portion of the cartridge including a first needle assembly having a first needle and a first capture member and a second needle assembly having a second needle and a second capture member; and an actuator movably coupled to the handle, the actuator including a first arm having a first deformable portion and a first coupling portion movably disposed in the first channel, the first deformable portion configured to deform in response to a force exerted on the first arm to move the first coupling portion within the first channel, the first coupling portion being operably coupled to the first needle assembly when the cartridge is coupled to the handle such that movement of the first coupling portion from a first position to a second position transitions the first needle assembly from a first configuration in which the first capture member is spaced apart from the first needle to a second configuration in which the first capture member is engaged with the first needle, the actuator including a second arm having a second deformable portion and a second coupling portion movably disposed in the second channel, the second deformable portion configured to deform in response to a force exerted on the second arm to move the second coupling portion within the second channel, the second coupling portion being operably coupled to the second needle assembly when the cartridge assembly is coupled to the handle such that movement of the second coupling portion from a first position to a second position transitions the second needle assembly from a first configuration in which the second capture member is spaced apart from the second needle to a second configuration in which the second capture member is engaged with the second needle.

13. The apparatus of claim 12, wherein the first arm and the second arm are each pivotably coupled to the handle.

14. The apparatus of claim 12, wherein the handle defines a longitudinal axis, the first coupling portion configured to move in the first channel in a direction parallel to the longitudinal axis of the handle, the second coupling portion configured to move in the second channel in a direction parallel to the longitudinal axis of the handle.

15. The apparatus of claim 12, further comprising:

a lock operably coupled to the actuator, the lock configured to selectively limit movement of the first coupling portion and the second coupling portion.

16. The apparatus of claim 15, wherein the actuator includes a selector coupled to the lock, the selector configured to transition between a first configuration in which the lock limits movement of the first coupling portion and a second configuration in which the lock limits movement of the second coupling portion.

17. The apparatus of claim 12, wherein the first needle is coupled to a first end of a suture, the first needle configured to advance a portion of the suture through an engagement portion of a target tissue when the first needle assembly is transitioned from the first configuration to the second configuration, the second needle is coupled to a second end of the suture, the second needle configured to advance a portion of the suture through a coupling portion of the target tissue when the second needle assembly is transitioned from the first configuration to the second configuration, the cartridge configured to place a single suture in the target tissue.

18. An apparatus, comprising:
a cartridge having a proximal end portion and a distal end portion, the proximal end portion of the cartridge configured to be coupled to a handle, the distal end portion of the cartridge including a needle assembly and defining a rotational axis, the needle assembly including a needle and an capture member,
at least a portion of the needle assembly configured to deform to rotate the needle and the capture member about the rotational axis from a first configuration in which the needle and the capture member are spaced apart to a second configuration in which the capture member engages the needle, wherein the needle assembly includes a needle cam, the needle of the needle assembly being at least temporarily coupled to the needle cam,
the needle assembly configured to be transitioned from the second configuration to a third configuration, the capture member configured to engage the needle to decouple the needle from the needle cam as the needle assembly is transitioned from the second configuration to the third configuration.

19. The apparatus of claim 18, wherein the proximal end portion of the cartridge is configured to be one of fixedly coupled to the handle or removably coupled to the handle.

20. The apparatus of claim 18, wherein the cartridge includes a push rod having a proximal end portion and a distal end portion, the distal end portion of the push rod being coupled to the needle assembly.

21. The apparatus of claim 18, wherein the cartridge includes a push rod having a proximal end portion and a distal end portion, the distal end portion of the push rod is coupled to the needle assembly,
the proximal end portion of the push rod configured to be coupled to an actuator when the proximal end portion of the cartridge is coupled to the handle, the push rod configured to exert a force to transition the needle assembly from the first configuration to the second configuration in response to an actuation of the actuator.

22. The apparatus of claim 18, wherein at least a portion of the cartridge is disposed in an elongate housing, the elongate housing having a surface, the rotational axis defined by the needle assembly being parallel to the surface of the elongate housing in at least one plane.

23. The apparatus of claim 22, wherein the rotational axis is spaced apart from the surface of the elongate housing.

24. The apparatus of claim 18, wherein the needle assembly includes a needle cam, the needle of the needle assembly being at least temporarily coupled to the needle cam, the needle cam being monolithically formed with the capture member.

25. The apparatus of claim 24, wherein the deformation of the portion of the needle assembly rotates the needle cam about the rotational axis in a first rotational direction and rotates the capture member about the rotational axis in a second rotational direction opposite the first rotational direction.

26. The apparatus of claim 18, wherein at least a portion of the needle assembly forms a living hinge.

27. The apparatus of claim 18, wherein the needle assembly is a first needle assembly, the needle is a first needle, the capture member is a first capture member, the distal end of the cartridge further includes a second needle assembly having a second needle and a second capture member, at least a portion of the second needle assembly configured to deform to rotate the second needle and the second capture member about the rotational axis from a first configuration in which the second needle and the second capture member are spaced apart to a second configuration in which the second capture member engages the second needle.

28. The apparatus of claim 18, wherein the cartridge is from a plurality of cartridges, the plurality of the cartridges and the handle being disposed in a substantially sealed package prior to use.

29. An apparatus, comprising:
a handle having a proximal end portion and a distal end portion;
a cartridge having a proximal end portion and a distal end portion, the proximal end portion configured to be removably coupled to the distal end portion of the handle, the distal end portion of the cartridge having a first needle assembly and a second needle assembly each configured to be transitioned between a first configuration and a second configuration, the first needle assembly including a first needle and a first capture member, the second needle assembly including a second needle and a second capture member;
an actuator movably coupled to the handle, the actuator having a first coupling portion operably coupled to the first needle assembly when the cartridge is coupled to the handle and a second coupling portion operably coupled to the second needle assembly when the cartridge is coupled to the handle, the first coupling portion configured to move relative to the handle in response to a first force to transition the first needle assembly from the first configuration in which the first capture member is spaced apart from the first needle to the second configuration in which the first capture member engages the first needle, the second coupling portion configured to move relative to the handle in response to a second force to transition the second needle assembly from the first configuration in which the second capture member is spaced apart from the second needle to the second configuration in which the second capture member engages the second needle, wherein the actuator includes a first arm and a second arm, the first coupling portion included in the first arm, the second coupling portion included in the second arm, wherein the first force is exerted on the first arm, a portion of the first arm is configured to deform in response to the first force, the first coupling portion being moved relative to the handle as the portion of the first arm deforms, the second force is exerted on the second arm, a portion of the second arm is configured to deform in response to the second force, the second coupling portion being moved relative to the handle as the portion of the second arm deforms; and
a lock operably coupled to the actuator, the lock configured to selectively limit movement of the first coupling portion and the second coupling portion.

* * * * *